(12) United States Patent
Frey, II et al.

(10) Patent No.: US 7,786,166 B2
(45) Date of Patent: Aug. 31, 2010

(54) METHODS AND COMPOSITIONS FOR PROTECTING AND TREATING MUSCARINIC RECEPTORS THROUGH ADMINISTRATION OF AT LEAST ONE PROTECTIVE AGENT

(75) Inventors: William H. Frey, II, White Bear Lake, MN (US); John Randall Fawcett, Palo Alto, CA (US)

(73) Assignee: Healthpartners Research Foundation, Bloomington, MN (US)

( * ) Notice: Subject to any disclaimer, the term of this patent is extended or adjusted under 35 U.S.C. 154(b) by 968 days.

(21) Appl. No.: 11/220,116

(22) Filed: Sep. 6, 2005

(65) Prior Publication Data

US 2006/0009414 A1   Jan. 12, 2006

Related U.S. Application Data

(62) Division of application No. 09/844,450, filed on Apr. 27, 2001, now Pat. No. 7,084,126.

(60) Provisional application No. 60/200,843, filed on May 1, 2000, provisional application No. 60/230,263, filed on Sep. 6, 2000, provisional application No. 60/233,025, filed on Sep. 15, 2000.

(51) Int. Cl.
 *A61K 31/35*   (2006.01)
(52) U.S. Cl. ...................... 514/454; 514/456
(58) Field of Classification Search ........................ None
See application file for complete search history.

(56) References Cited

U.S. PATENT DOCUMENTS

| | | | |
|---|---|---|---|
| 5,082,833 A | 1/1992 | Shamsuddin | |
| 5,135,923 A | 8/1992 | Siren | |
| 5,939,395 A | 8/1999 | Yu et al. | |
| 6,576,660 B1 * | 6/2003 | Liao et al. | 514/456 |
| 7,618,615 B2 * | 11/2009 | Frey et al. | 424/9.1 |

FOREIGN PATENT DOCUMENTS

| | | |
|---|---|---|
| JP | 61263902 A | 11/1986 |
| WO | WO 90/00057 A | 1/1990 |
| WO | WO 97/22251 A | 6/1997 |

OTHER PUBLICATIONS

Frey et al., "delivery of 125I-NGF to the Brain via the Olfactory Route", Drug Delivery, 4:87-92, 1997.*
Doyle et al., Journal of Cerebral Blood Flow & Metabolism, 2008(28), 1235-1248.*
Liu et al., Molecular and Cellular Biology, Sep. 1992, 3978-3990.*
The Merck Index, Twelfth Edition, 1996, entries 3908 and 7135.
Venters Jr., Homer D. et al., "Heme from Alzheimer's brain inhibits muscarinic receptor binding via thiyl radical generation" Brain Research, 1997, 764, 93-100.
Kornberg, Arthur, et al.; "Inorganic Polyphosphate: A Molecule of Many Functions"; Annual Review Biochemistry, vol. 68: 89-125; Annual Reviews; US 1999.
Frey II, William H. et al.; "Brain Research 714 (1996) 87-94: Endogenous Alzheimer's brain factor and oxidaized glutathione inhibit antagonist binding to the muscarinic receptor"; Elsevier Science B.V.; US 1996.
Frey II, William H. et al.; "Brain Research 655 (1994) 153-160: Inhibitor of antagonist binding to the muscarinic receptor is elevated in Alzheimer's brain"; Elsevier Science B.V.; US 1994.
Otterbein, Leo E., et al.; "Invited Review: Heme oxygenase: colors of defense against cellular stress"; The American Physiological Society; www.aiplung.org: US 2000.

* cited by examiner

*Primary Examiner*—Traviss C McIntosh, III
(74) *Attorney, Agent, or Firm*—Altera Law Group, LLC

(57) ABSTRACT

Methods and compositions for protecting muscarinic receptor(s) in a subject by administering at least one protective agent alone, in combination with other protective agents, or in combination with at least one neurologic agent.

32 Claims, 20 Drawing Sheets

Guanylimidodiphosphate Protects the mAChR from Inactivation by the LMW Inhibitor
(n = 4)

$P_{max} = 103 \pm 5\%$
$P_{50} = 4 \pm 2\ \mu M$
$r^2 = 0.99$

Percent Protection of $^3$H-QNB Binding vs [Gpp(NH)p] μM

FIGURE 5

METHODS AND COMPOSITIONS FOR PROTECTING AND TREATING MUSCARINIC RECEPTORS THROUGH ADMINISTRATION OF AT LEAST ONE PROTECTIVE AGENT

CROSS-REFERENCE TO RELATED APPLICATIONS

This application is a divisional application of prior application Ser. No. 09/844,450 filed Apr. 27, 2001, now U.S. Pat. No. 7,084,126, and claims the benefit of provisional application No. 60/200,843 filed May 1, 2000; provisional application No. 60/230,263 filed Sep. 6, 2000; and provisional application No. 60/233,025 filed Sep. 15, 2000; each entitled "Method and Compositions for Enhancing Cellular Function and Protecting Receptor."

BACKGROUND OF THE INVENTION

Cellular function depends on the maintenance of intact cellular components including: receptors, proteins, lipids, nucleic acids, carbohydrates, hormones and cofactors. Cellular receptors, including cell surface receptors, mediate communication within and between cells, tissues and organs within a living system. Cellular receptors also provide a means to signal a living system, tissues, organs, cells, and subcellular compartments. Receptors are molecules or macromolecules that bind or interact with agents to alter or enhance their function. Many receptors are membrane bound proteins, which require not only that their protein structure be intact but also that the membrane lipids and carbohydrates be intact and functional. Through various signaling mechanisms, the messages sent by the receptor, either in the presence or absence of an interacting or bound agent, can be transmitted. Following receptor activation, signalling also requires intact cellular proteins, lipids, nucleic acids and carbohydrates in order for the message to be properly received.

Often as a result of damage, the ability of cellular receptors to interact with or bind various agents is decreased, resulting in an impairment of vital intrinsic and extrinsic communication. Damage to cellular receptors and other cellular components diminishes the ability of a receptor to bind agents and elicit a communication or signaling event. This can result in damage or death to cells, resulting in damage or diseases of tissues, organs and living systems. Accordingly, there is a need for a means to protect receptors and other cellular components from damage and to increase the efficacy of agents that exert their effects through cellular receptors.

SUMMARY OF THE INVENTION

The invention provides methods for enhancing cellular function through protection of tissue components and/or increasing the efficacy of a therapeutic agent in a subject in need thereof. The method includes administering a composition, such as a pharmaceutical composition, of a pyrophosphate analog. In a second embodiment, the method includes administering a composition, such as a pharmaceutical composition, of a protective agent.

Preferably, the invention provides a method for protecting a muscarinic acetylcholine receptor (mAChR) and/or increasing the efficacy of an agent that directly or indirectly affects a mAChR in a subject in need thereof. Suitable agents that directly or indirectly affect a muscarinic receptor include anticholinesterase agents, muscarinic agonists, allosteric regulators of a muscarinic receptor, muscarinic antagonists, and neurotrophic and neuritogenic factors that are similar to naturally occurring nerve growth promoting substances. In one embodiment, the invention provides a method to protect a mAChR and/or increase the efficacy of agents that directly or indirectly affect a mAChR in the central nervous system (CNS) of a subject in need thereof. Preferably, a muscarinic receptor is protected from an endogenous low molecular weight inhibitor from Alzheimer's brain tissue, a metal, or oxidative stress. In another embodiment, the invention provides a method to protect a mAChR and/or increase the efficacy of agents that directly or indirectly affect a mAChR not in the CNS of a subject in a need thereof. In a first embodiment, the method includes administering a pyrophosphate analog. In a second embodiment, the method includes administering a protective agent.

The invention also provides a method for increasing the efficacy of a therapeutic agent, preferably a neurologic agent, in a subject in need thereof. In a first embodiment, this method includes administering a pyrophosphate analog. In this embodiment, the increased efficacy of the neurologic agent preferably results from protection of a muscarinic receptor caused or induced by the pyrophosphate analog. In a second embodiment, this method includes administering a protective agent. In this second embodiment, the increased efficacy of the neurologic agent preferably results from protection of a muscarinic receptor caused or induced by the protective agent. In each embodiment, the subject preferably is concurrently receiving, has recently received, or will soon receive a neurologic agent such as nerve growth factor (NGF), insulin growth factor (IGF-1), brain derived neurotrophic factor (BDNF), fibroblast growth factor (FGF), and the like; certain other known neurotrophins and neuroprotectants; and medications used for stroke, Alzheimer's disease, Parkinson's disease, ALS, traumatic brain or spinal cord injury, cancer, diabetes, neuropathies, hypertension, irritable bowel syndrome; diseases or disorders of the heart and smooth muscles, blood, blood vessels, glands or bones and other disorders. Preferably, the therapeutic agent directly or indirectly affects a mAChR. Such agents include an anticholinesterase agent, a muscarinic agonist, and a muscarinic antagonist.

Pyrophosphate analogs that can be employed in the appropriate embodiment of the method of the invention include compounds of Formula I:

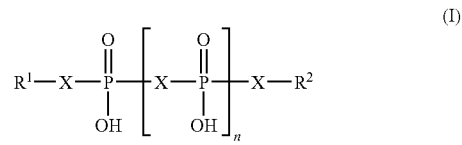

where each X is independently O, $CH_2$, NH, or S; $R^1$ is H, a small alkyl group, guanyl, adenylyl, glycerol, acyl glycerol, diacyl glycerol, serine, threonine, tyrosine, arachidonyl, —$PO(OH)(OR^2)$, or —$(PO(OH)O)_m$—$PO(OH)(OR^1)$, and m is 1-3; $R^2$ is H, a small alkyl group, guanyl, adenylyl, glycerol, acyl glycerol, diacyl glycerol, serine, threonine, tyrosine, or arachidonyl; and n is 1-900. Compounds of Formula I in which $R^1$ is a small alkyl group, guanyl, adenylyl, glycerol, acyl glycerol, diacyl glycerol, serine, threonine, arachidonyl, —$PO(OH)(OR^2)$, or —$(PO(OH)O)_m$—$PO(OH)(OR^2)$; or $R^2$ is a small alkyl group, guanyl, adenylyl, glycerol, acyl glycerol, diacyl glycerol, serine, threonine, tyrosine, or arachidonyl can be referred to as substituted pyrophosphate analogs. Compounds of Formula I can also include substituted pyrophosphate analogs such as a dinucleoside-5-5'-pyrophosphate, a cyclopyrophosphate of purine, and a pyrimidine acyclonucleoside. The compound of Formula I can be any pharmaceutically acceptable salt or basic addition salt. Preferably, X is O, CH$_2$, NH, or S; R$^1$ is H; R$^2$ is H; and n is 1-6. More preferably the pyrophosphate analog is pyrophosphate or imidodiphosphate.

Additional pyrophosphate analogs include compounds of Formula II:

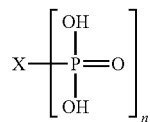

where n=2-4; X is O, RCR$^1$; CR; C (n=4), CH (n=3), or CH$_2$ (n=2); NH; N; S; and R and/or R$^1$ is H, OH, a small alkyl group, such as CH$_3$ or (CH$_2$)$_m$NH$_2$ where m=1-6. Further included are bisphosphonic acids, which are also known as bisphosphonates, where X is preferably RCR$^1$, where R and R$^1$ groups are chosen independently from OH, H$_2$N(CH$_2$)$_2$, or CH$_3$. For example, RCR$^1$ can be H$_2$N(CH$_2$)$_2$C(OH) or CH$_3$COH. More specifically, the bisphosphonates include etidronic acid ((1-Hydroxyethylidene)bisphosphonic acid) and pamidronic acid ((3-Amino-1-hydroxypropylidene)bisphosphonic acid) where preferably n=2.

Yet more additional pyrophosphate analogs include substituted pyrophosphate analogs such as an inositol diphosphate, an inositol triphosphate, an inositol tetraphosphate, an inositol pentaphosphate, and an inositol hexaphosphate.

Suitable protective agents that can be employed in an embodiment of the method of the invention include a bilirubin, biliverdin, carnosol, quercetin, myricetin, a bioflavinoid, a combination thereof, or a pharmaceutically acceptable salt thereof; a heme binding compound, such as hemopexin, lipopexin, a lipoprotein, or ApoE-2; and a heme oxygenase, such as heme oxygenase-1 or heme oxygenase-2, biliverdin reductase, a catalase, a peroxidase, a vector encoding a biliverdin reductase, a vector encoding a heme oxygenase (e.g. a vector encoding a heme oxygenase-1 or a vector encoding a heme oxygenase-2), a vector encoding a catalase, a vector encoding a peroxidase, or a combination thereof. Biliverdin reductase can be administered alone or in combination with a heme oxygenase. Heme oxygenases include recombinant heme oxygenase. Preferably, a heme oxygenase is a human heme oxygenase.

The method of the invention can treat or prevent a CNS disorder. Preferably, the method of the invention can treat or prevent neurodegeneration, can improve memory and cognition, can treat or prevent brain deterioration or cognitive and memory loss associated with aging, or can treat or prevent Alzheimer's Disease, Parkinson's disease, Lewy body dementia, multiple sclerosis, cerebellar ataxia, progressive supranuclear palsy, amyotrophic lateral sclerosis, affective disorders, anxiety disorders, and/or schizophrenia; nerve damage from cerebrovascular disorders such as stroke or atherosclerosis in the brain or spinal cord, from CNS infections including meningitis and HIV, from tumors of the brain and spinal cord, prion diseases, and CNS disorders resulting from ordinary aging (e.g., anosmia), brain injury, or spinal cord injury.

In another embodiment, the method of the invention can treat or prevent a disease or disorder not of the CNS. Preferably, the method of the invention can treat or prevent cancer, or neuropathies or diseases or disorders of the heart, smooth muscles, blood, blood vessels, glands, or bones. Such diseases or disorders include hypertension, myocardial infarction, ischemic heart disease, congestive heart failure, cardiac arrhythmias, cancer, irritable bowel syndrome, diverticular disease, urinary incontinence, esophageal achalasia, chronic obstructive airways disease, xerostomia, diabetes mellitus, Sjogren's syndrome or dry eye syndrome which involves decreased secretion of tears by, for example, the lacrimal glands, Paget's disease, hereditary hematochromatosis or a non-CNS disorder resulting from normal aging.

In another embodiment, the method of the invention treats infections, including (without limitation) bacterial, fungal, algo, or algae infections. Such infections can occur in plants (for which a preferred embodiment of the invention employs imidodiphosphate as the pyrophosphate analog), animals, or mammals.

BRIEF DESCRIPTION OF THE FIGURES

FIG. 5 illustrates protection of a mAChR by guanylimidodiphosphate. Guanylimidodiphosphate protected the mAChR from inactivation by the endogenous low molecular weight inhibitor. Guanylimidodiphosphate protected the receptor from loss of antagonist ($^3$H-QNB) binding.

DETAILED DESCRIPTION OF THE INVENTION

Definitions

Figure 1:
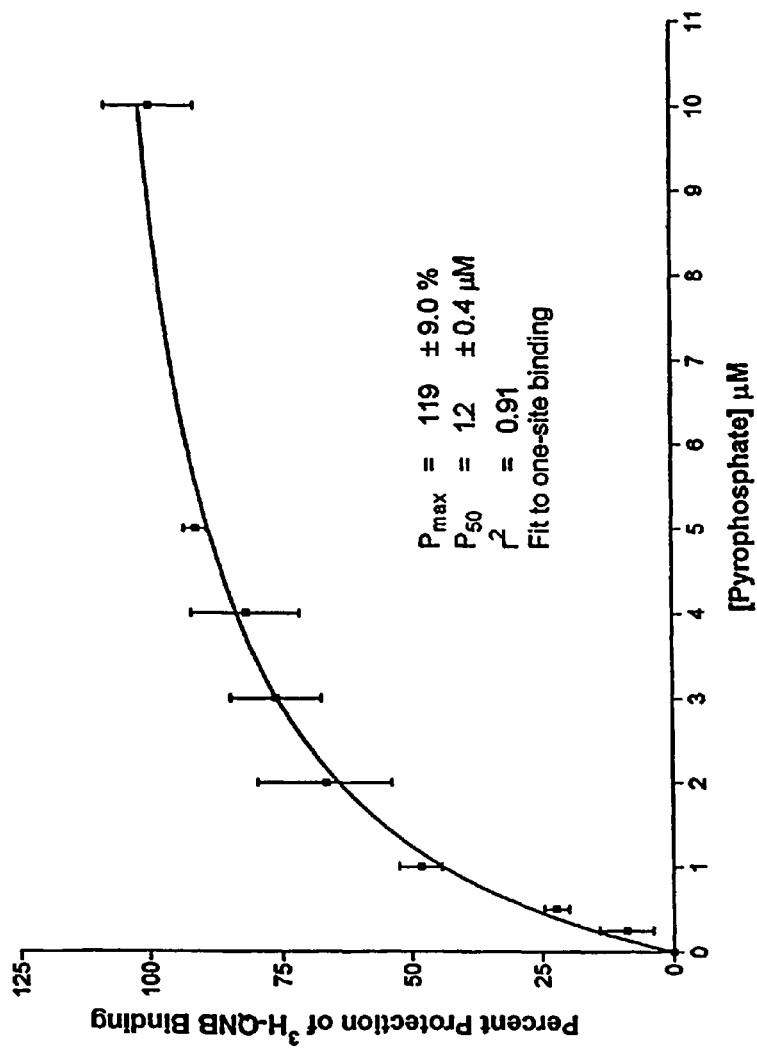
FIG. 1 illustrates protection of a mAChR by pyrophosphate. Pyrophosphate protected the mAChR from inactivation by the endogenous low molecular weight inhibitor. Pyrophosphate protected the receptor from loss of antagonist ($^3$H-QNB (quinulidinyl benzilate)) binding.
Figure 2:
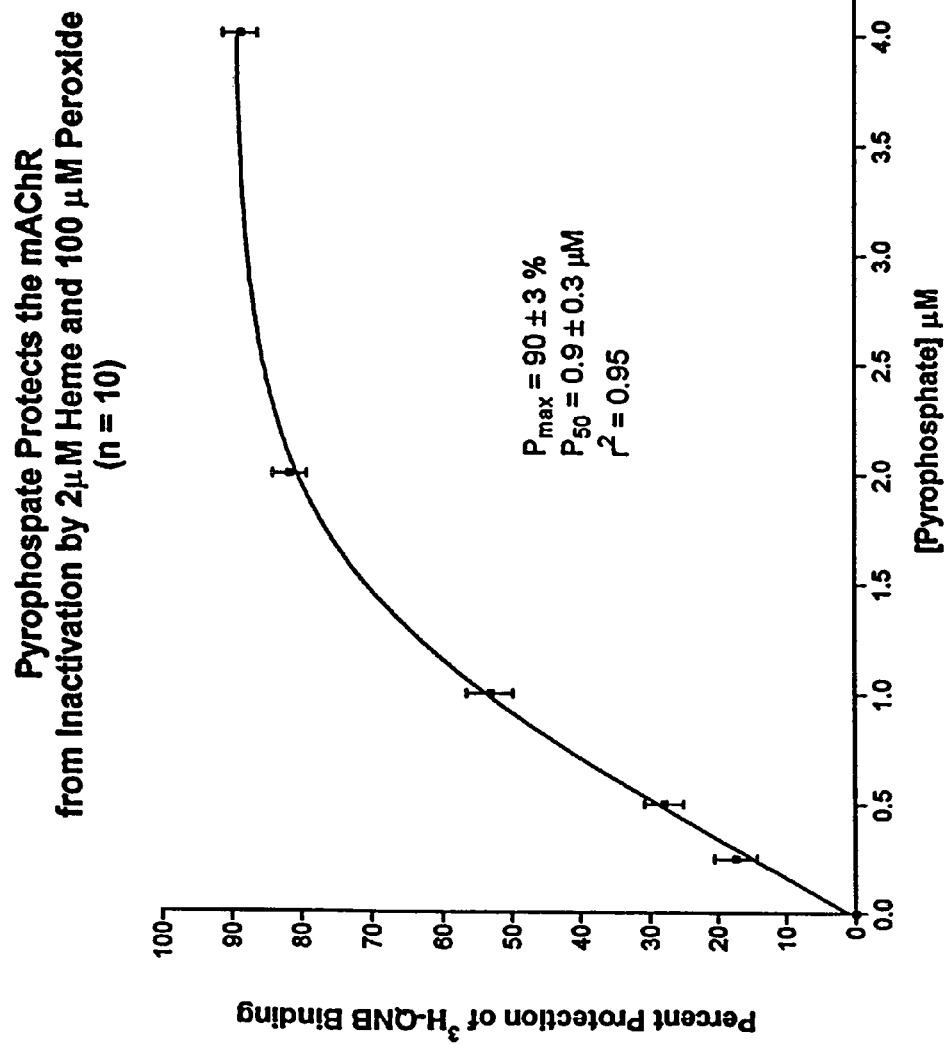
FIG. 2 illustrates protection of a mAChR by pyrophosphate. Pyrophosphate protected the mAChR from inactivation by heme and peroxide. Pyrophosphate protected the receptor from loss of antagonist ($^3$H-QNB) binding.

As used herein, "cholinesterase" refers to an enzyme capable of hydrolyzing acetylcholine and includes acetylcholinesterase.

As used herein, "agonist" refers to an agent that binds to or interacts with a receptor and elicits a response transduced through the receptor. Agonist includes full agonists, partial agonists, and inverse agonists. A full agonist is an agent that can elicit a maximal response from a receptor. A partial agonist is an agent that can elicit, at best, a less than maximal response from a receptor. An inverse agonist is an agent that produces a response that is opposite that of a full or partial agonist. For example, if agonist binding or interaction with a receptor results in increased concentration of cAMP within a cell, then inverse agonist binding or interaction with the same receptor will result in a decreased concentration of cAMP within the cell.

As used herein, "antagonist" refers to an agent that is capable of partially or completely inhibiting, or reversing, the effect of an agonist on a receptor.

As used herein, "allosteric modifier" refers to an agent that binds or interacts with a site other than the agonist binding site of a receptor and modifies the ability of an agonist or an antagonist to elicit or inhibit, respectively, a response transduced through a receptor, without itself eliciting a response.

As used herein, "tissue component" includes receptors, proteins, lipids, nucleic acids, carbohydrates, hormones, vitamins, and cofactors.

As used herein, "receptor" refers to any molecule or macromolecule within or on a cell that interacts with another molecule or macromolecule to confer a response or transduce a signal and includes nuclear receptors, mitochondrial receptors, cytoplasmic receptors, and cell surface receptors. Receptors include receptors for neurotrophins (including, without limitation, nerve growth factor, neurotrophins 3, 4, and/or 5 (NT-3, NT-4 and/or NT-5) and brain derived growth factors); neurotransmitters; hormones; steroids; local mediators such as nitric oxide, carbon monoxide, histamine, and growth factors like insulin, insulin-like growth factor-I, fibroblast growth factors, ciliary neurotrophic factor, glia-derived neurotrophic factor, glia-derived nexin, cholinergic enhancing factor, transforming growth factors, activity dependent neurotrophic factor, neurokines, gangliosides, phosphatidylserine, PDGF (platelet derived growth factor) and EGF (epidermal growth factor); benzodiazepines; arachidonic acid; purines (including, without limitation, adenosine and ATP); nucleotides and cyclic nucleotides; calcium and other divalent cations; odorants; antisense oligonucleotides; opiates; cannabinoids; glutamate; melatonin; angiotensin II; secretin; vasoactive intestinal peptide; cholecystokinin; ACTH; vasopressin; thrombin; ion channels; and the like. Receptors also include but are not limited to G-protein-coupled receptors, ion-channel-linked receptors and enzyme-linked receptors.

As used herein, "protecting a receptor" refers to protecting the physical integrity of a receptor and/or the function of a receptor, such as enhancing the function of a receptor; or maintaining the ability of the receptor to respond to agonists, to respond to antagonists, to transmit a message to the interior of a cell, or to send a signal within a cell, cell nucleus, or mitochondria.

As used herein, "central nervous system" (CNS) refers to the brain and spinal cord and associated tissues.

As used herein, "disorders and diseases of the CNS" refers to brain diseases such as Alzheimer's disease, Parkinson's disease, Lewy body dementia, multiple sclerosis, cerebellar ataxia, progressive supranuclear palsy, amyotrophic lateral sclerosis, affective disorders, anxiety disorders, and/or schizophrenia; cell damage; nerve damage from cerebrovascular disorders such as stroke in the brain or spinal cord, from CNS infections including meningitis and HIV, from tumors of the brain and spinal cord, prion diseases, and CNS disorders resulting from ordinary aging (e.g., anosmia), brain injury, or spinal cord injury.

As used herein, a disease or disorder that relates to or is caused at least in part by dysfunction, alteration, or loss of one or more G-protein coupled receptors refers to Alzheimer's disease; Parkinson's disease; drug addiction, such as opiate addiction or cannabinoid abuse; pain; Sjogren's or dry eye syndrome; heart diseases including congestive heart failure, myocardial infarction, cardiac arrhythmia; diseases of smooth muscle organs or glands such as irritable bowel syndrome, colitis, hypertension, erectile dysfunction, diabetes, obesity, blood coagulation disorders; and the like.

An "effective amount" of agent is an amount sufficient to prevent, treat, reduce and/or ameliorate the symptoms and/or underlying causes of any of the above disorders or diseases. In some instances, an "effective amount" is sufficient to eliminate the symptoms of those diseases and, perhaps, overcome the disease itself. Preferably, an effective amount of an agent yields a tissue concentration in the range of about $10^{-7}$ molar to about $10^{-5}$ molar, but the concentrations may be greater provided that toxicity is avoided.

In the context of the present invention, the terms "treat" and "therapy" and the like refer to alleviate, slow the progression, prophylaxis, attenuation or cure of existing disease. Prevent, as used herein, refers to putting off, delaying, slowing, inhibiting, or otherwise stopping, reducing or ameliorating the onset of such diseases or disorders. It is preferred that a large enough quantity of the agent be applied in non-toxic levels in order to provide an effective level of activity against the disease. The method of the present invention may be used with any animal, such as a mammal or a bird (avian), more preferably a mammal. Poultry are a preferred bird. Exemplary mammals include, but are not limited to rats, cats, dogs, horses, cows, sheep, pigs, and more preferably humans.

Protecting a Tissue Component

The invention provides a method for protecting any biomolecule or tissue component including a protein, a lipid, a nucleic acid, a carbohydrate, a hormone and the like. The invention is best illustrated, but is not limited to, the example of the protection of a receptor, preferably a muscarinic receptor, preferably a mAChR. In a first embodiment, the method includes administering a pyrophosphate analog. In a second embodiment, the method includes administering a protective agent. Protecting a receptor includes protecting the physical integrity of a receptor and/or the function of a receptor, such as maintaining the ability of the receptor to respond to agonists, to respond to antagonists, to transmit a message to the interior of a cell, or to send a signal within a cell, cell nucleus, or mitochondria.

An embodiment of the invention provides a method for protecting a receptor from free radical damage. Free radicals and other reactive oxygen species (e.g., $H_2O_2$, HOCl, and radicals such as $O_2^-$, sulfur cation, nitric oxide radical, ferryl, peroxyl, peroxynitrite, thiyl, thiylperoxyl, and alkoxyl) are highly reactive, and many free radical reactions are highly damaging to cellular components. Free radical reactions can crosslink proteins, mutagenize DNA, and peroxidize lipids. Such reactions can have deleterious effects on cellular receptors. Preferably, the method of the invention includes protection of a receptor, such as a mAChR, or of DNA, RNA, lipids, and proteins necessary for receptor function from deleterious effects.

In another embodiment, the invention provides a method for reducing or eliminating deleterious effects of an endogenous inhibitor found in elevated levels in the brains of Alzheimer's disease patients. This endogenous, low molecular weight inhibitor, as it is known, inhibits agonist and antagonist binding to mAChRs. This inhibitor has a molecular weight of less than 3500 Da and is believed to generate free radicals, in the presence of glutathione or other sulthydryl compounds, that irreversibly inhibit or inactivate the mAChR The inhibitor also contains free heme, which can generate free radicals, including superoxide radicals, peroxyl radicals, and thiyl radicals, and can cause neurotoxicity. Heme has been shown to damage protein and lipid components of membranes by Vincent (Oxidative Effects of Heme and Porphyrins on Proteins and Lipids, Seminars in Hematology 26(2): 105-113, 1989). Membrane lipid defects have been demonstrated in Alzheimer's disease by Ginsberg et al. (Evidence for a Membrane Lipid Defect in Alzheimer's Disease, Mol. and Chem. Neuropathol. 19: 37-46, 1993). In addition, heme has been proposed to contribute to atherosclerosis by Jacob (Newly recognized causes of atherosclerosis: The role of microorganisms and of vascular iron overload, J. Lab. Clin. Med. 123: 808-816, 1994).

In one embodiment, the method of the invention includes increasing the efficacy of an agent that directly or indirectly affects a mAChR. By way of example, administration of a pyrophosphate analog can increase the efficacy of a muscarinic agonist in the presence of the inhibitor. In another embodiment, the method of the invention includes reducing or eliminating deleterious effects the low molecular weight inhibitor or heme by decreasing or preventing the generation of free radicals or trapping radicals once formed.

Receptors

The invention provides a method for protecting a receptor and/or increasing the efficacy of agents that directly or indirectly affect a receptor. Such receptors include G-protein-coupled receptors, ion-channel-linked receptors and enzyme-linked receptors. Examples include receptors for neurotrophins; neurotransmitters; hormones; steroids; local mediators such as nitric oxide, histamine, and growth factors like PDGF (platelet derived growth factor) and EGF (epithelial growth factor); nucleotides and cyclic nucleotides; calcium and other divalent cations; odorants; antisense oligonucleotides; and the like. Preferably the receptor is a muscarinic receptor. Examples of G-protein coupled receptors include receptors that respond to odorants, opiates, cannabinoids, glutamate, melatonin, angiotensin II, secretin, vasoactive intestinal peptide (VIP), cholecystokinin (CCK), adrenaline (adrenergic receptors), acetylcholine (muscarinic receptors), ACTH, vasopressin, thrombin, and the like.

In one embodiment the invention provides a method for protecting a receptor and/or increasing the efficacy of agents that directly or indirectly affect a receptor in the CNS. In another embodiment, the invention provides a method for protecting a receptor and/or increasing the efficacy of agents that directly or indirectly affect a receptor not in the CNS. Agents whose efficacy are increased by the method of the invention include receptor agonists, allosteric modifiers of receptors, and receptor antagonists.

An embodiment of the invention provides a method for treating or preventing a disease or disorder that relates to or is caused at least in part by dysfunction, alteration, or loss of one or more G-protein coupled receptors. These diseases and disorders include Alzheimer's disease; Parkinson's disease; stroke; multiple sclerosis; ALS; drug addiction, such as opiate addiction or cannabinoid abuse; pain; Sjogren's or dry eye syndrome; heart diseases including congestive heart failure, myocardial infarction, cardiac arrhythmia; cancer; diseases of smooth muscle organs or glands such as irritable bowel syndrome, colitis, hypertension, erectile dysfunction, diabetes, obesity, blood coagulation disorders; and the like.

Muscarinic Receptors

The invention provides a method for protecting a mAChR and/or increasing the efficacy of agents that directly or indirectly affect a mAChR. There are at least five pharmacological classes of mAChRs, including the M1, M2, and M3 muscarinic receptors, and several genetic subclasses including m1, m2, m3, m4, and m5. These muscarinic receptors are G-protein coupled receptors. Each receptor subtype has its own unique pattern of expression throughout various tissues. As such, dysfunction of each receptor subclass, or combinations thereof, may have deleterious effects leading to a variety of diseases or disorders. The method of the invention can provide protection to a muscarinic receptor in any or several mAChR subclasses, and therefore; can be of benefit to those at risk or suffering from diseases associated with dysfunction of one or more muscarinic receptor subtype. Preferably, the method of the invention provides protection to M1 and M2 muscarinic receptors.

Muscarinic receptors mediate numerous of the inhibitory and excitatory effects of the neurotransmitter acetylcholine in the heart, smooth muscle, blood vessels, glands and in neurons (both presynaptic and postsynaptic) in the autonomic and the central nervous system. Dysfunction of mAChRs thus can contribute to a variety of diseases and/or disorders. Through protection of a mAChR and/or through increasing the efficacy of agents that directly or indirectly affect a mAChR, the method of the invention can provide benefit to subjects suffering from or at risk of a disease or disorder associated with mAChR dysfunction.

An embodiment of the invention provides a method for protecting a mAChR and/or increasing the efficacy of agents that directly or indirectly affect a mAChR in the nervous system of a subject, and therefore, can be of benefit to subjects suffering from or at risk of central nervous system or peripheral nervous system disorders. For example, mAChRs and other receptors are involved in the regulation of the function of cells throughout the CNS. Accordingly, the method of the invention can provide benefit to subjects suffering from or at risk of CNS disorders such as Alzheimer's disease, Parkinson's disease, Lewy body dementia, multiple sclerosis, cerebellar ataxia, progressive supranuclear palsy, amyotrophic lateral sclerosis, affective disorders, anxiety disorders, and/or schizophrenia; nerve damage from cerebrovascular disorders such as stroke, from CNS infections including meningitis and HIV, from tumors of the brain and spinal cord, prion diseases, and CNS disorders resulting from ordinary aging, brain injury, or spinal cord injury. mAChRs are also involved in the regulation of the function of cells in the peripheral nervous system, including the autonomic nervous system. Accordingly, the method of the invention can provide benefit to subjects suffering from or at risk of peripheral nervous system disorders, such as peripheral neuropathy, including that associated with diabetes. For example, in diabetic patients nerves can deteriorate as blood vessels that contain muscarinic or other receptors are lost. Preferably, the method of the invention can benefit a subject suffering from or at risk of Alzheimer's disease.

Another embodiment of the invention provides a method for protecting a mAChR and/or increasing the efficacy of agents that directly or indirectly affect a mAChR not within the nervous system of a subject, and therefore, can be of benefit to subjects suffering from or at risk of disease or disorder outside the nervous system. For example, mAChRs are involved in the regulation (e.g., stimulation or inhibition) of smooth muscle contraction, the regulation of heart rate and cardiac contractility, the regulation of secretion of enzymes or hormones, including the release of amylase from the parotid gland and the release of digestive enzymes and insulin from the pancreas, the regulation of bone growth, and the regulation of iron metabolism. Accordingly, the method of the invention can provide benefit to subjects suffering from or at risk of smooth muscle related disorders such as irritable bowel syndrome, diverticular disease, urinary incontinence, esophageal achalasia, diseases or disorders of the blood vessels (e.g. hypertension), or chronic obstructive airways disease; heart muscle related disorders such as pathologic bradycardia or tachycardia, arrhythmia, flutter or fibrillation; blood related disorders such as hereditary hematochromatosis; bone disorders such as Paget's disease; cancer; and gland related disorders such as xerostomia, diabetes mellitus, or Sjogren's syndrome or dry eye syndrome which involves decreased secretion of tears by, for example, the lacrimal glands. For example, tear secretion is known to require muscarinic cholinergic stimulation and intact muscarinic receptors. Accordingly, protection of a mAChR and/or increasing the efficacy of an agent that directly or indirectly affects a mAChR can be of benefit to a subject suffering from Sjogren's syndrome or dry eye syndrome.

Protecting a muscarinic receptor can result in enhancing the effectiveness of agents that directly or indirectly affect a mAChR. Useful agents that affect a mAChR include, but are not limited to, anticholinesterase agents, muscarinic agonists, muscarinic antagonists, and other agents useful for treatment of diseases associated with dysfunction of muscarinic receptors, including neurodegenerative and other CNS disorders.

The method of the invention also provides enhanced efficacy of agents that do not act directly, or indirectly, with a mAChR. Such enhanced efficacy can be achieved, for example, through protection of a receptor, preferably a mAChR. Protecting a muscarinic receptor can result in enhancing the efficacy of agents that do not exert their action directly or indirectly on the muscarinic receptor. Such enhanced efficacy can be achieved through desirable effects on cells to which protection of muscarinic receptors provides benefit. Typically, cells that derive benefit from protection of a muscarinic receptor are cells that contain muscarinic receptors. Examples of cells that contain a mAChR include particular neurons, smooth muscle cells, and gland cells.

Cells that lack a muscarinic receptor but which interact with enzymes, hormones, and/or other compounds released from cells with a muscarinic receptor can derive benefit from protecting a muscarinic receptor. Examples of cells lacking a mAChR that can derive-benefit from protecting a mAChR include cells that are presynaptic or postsynaptic relative to cells that contain a mAChR and cells that can interact with enzymes, hormones, and/or other compounds released from cells that contain a mAChR.

Examples of this phenomenon include: Stimulation of $m_2$ receptors on presynaptic membranes increases the release of acetylcholine which can then stimulate nicotinic receptors on other post synaptic cells. Stimulation of mAChR releases arachidonic acid, which can then affect a variety of other nearby brain cells. Arachidonic acid also increases secretion of amyloid precursor protein. Emmerling, M. R. et al. (1996) Ann. N.Y. Acad. Sci. 777:310-315. Activation of m1 and m3 mAChR attenuates release of amyloid B protein. Hung, A. Y. et al. (1993) J. Biol. Chem. 268:22959-22962. Stimulation of mAChR is required for memory and learning which also involve the proper function of noncholinergic cells. Stimulation of mAChR can increase the nitric oxide—cyclic GMP signaling system in neurons (Bauer, M. B. (1994) Neuroscience 62:351-359) and nitric oxide can travel from one cell to another to produce its effects. Stimulation of mAChRs markedly increase hippocampal BDNF and NGF in RNA levels. Once produced, these neurotrophins can produce important effects on other nerve cells in the brain. M. da Penha Berzaghi (1993) J. Neuroscience 13(9) 3818-3826.

By way of further example, some cells containing a mAChR in the pancreas can release insulin. Released insulin can then interact with cells in close proximity to, or at relatively great distances from, the cell from which it was released. Protection of a mAChR on a cell in the pancreas that releases insulin can have beneficial effects on a cell that interacts with insulin. Thus, cells lacking a mAChR can benefit from protection of a mAChR. Similarly, the efficacy of agents acting on cells lacking a mAChR can be enhanced by the method of the invention.

By way of yet further example, stimulation of mAChR in certain brain cells increases potassium ion evoked release of the neurotransmitter dopamine which then goes on to affect other brain cells having dopamine receptors. Joseph, J. A. et al. (1995) Brain Res. 673:195-193. Thus, CNS cells lacking a mAChR can benefit from protection of a mAChR. Similarly, the efficacy of agents acting on CNS cells lacking a mAChR can be enhanced by the method of the invention.

Pyrophosphate Analogs

In one embodiment, the method of the invention provides protection to a receptor and/or increases the efficacy of agents by administering to a subject a pyrophosphate analog. Useful pyrophosphate analogs include compounds of Formula I:

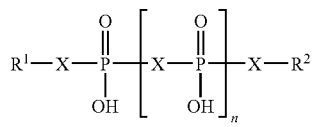

(I)

where each X is independently O, $CH_2$, NH, or S; $R^1$ is H, a small allyl group, guanyl, adenylyl, glycerol, acyl glycerol, diacyl glycerol, serine, threonine, tyrosine, arachidonyl, —PO(OH)($OR^2$), or —(PO(OH)O)$_m$—PO(OH)($OR_2$), and m is 1-3; $R^2$ is H, a small alkyl group, guanyl, adenylyl, glycerol, acyl glycerol, diacyl glycerol, serine, threonine, tyrosine, or arachidonyl; and n is 1-900. Compounds of Formula I in which $R^1$ is a small alkyl group, guanyl, adenylyl, glycerol, acyl glycerol, diacyl glycerol, serine, threonine, arachidonyl, —PO(OH)($OR^2$), or —(PO(OH)O)$_m$—PO(OH)($OR^2$); or $R^2$ is H, guanyl, adenylyl, glycerol, acyl glycerol, diacyl glycerol, serine, threonine, tyrosine, or arachidonyl can be referred to as substituted pyrophosphate analogs. Compounds of Formula I can also include substituted pyrophosphate analogs such as dinucleoside-5-5'-pyrophosphates, cyclophosphates of purine and pyrimidine acyclonucleosides. The compound of Formula I can be any pharmaceutically acceptable salt or basic addition salt. Preferably, X is O, $CH_2$, NH, or S; $R^1$ is H; and n is 2-6. More preferably the pyrophosphate analog is pyrophosphate or imidodiphosphate.

Additional preferred compounds of Formula I include pyrophosphate, glycerol pyrophosphate, arachidonylpyrophosphate, imidodiphosphate, serine phosphate, serine imidophosphate, threonine phosphate, threonine imidophosphate, guanylimidodiphosphate and adenylylimidodiphosphate. More preferably compounds of Formula I include pyrophosphate, imidodiphosphate, guanylimidodiphosphate and adenylylimidodiphosphate.

Additional pyrophosphate analogs include compounds of formula II:

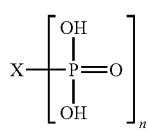

(II)

where n=2-4; X is O; $RCR^1$; CR; C (n=4), CH (n=3), or $CH_2$ (n=3); NH; N; S; and R and/or $R^1$ is H, OH, a small alkyl group (such as $CH_3$), or $(CH_2)_mNH_2$ where m=1-6. Further included are bisphosphonic acids, which are also known as bisphosphonates, where X is preferably $RCR^1$ and R and $R^1$ groups are chosen independently from OH, $H_2N(CH_2)_2$, or $CH_3$. For example, $RCR^1$ can be $H_2N(CH_2)_2C(OH)$ or $CH_3COH$. More specifically, the bisphosphonates include etidronic acid ((1-Hydroxyethylidene)bisphosphonic acid) and pamidronic acid ((3-Amino-1-hydroxypropylidene)bisphosphonic acid) where preferably n=2.

Yet more additional pyrophosphate analogs include substituted pyrophosphate analogs such as inositol diphosphate, inositol triphosphate, inositol tetraphosphate, inositol pentaphosphate, and inositol hexaphosphate.

Such pyrophosphate and imidodiphosphate compounds and the like can be prepared as basic addition salts, such as sodium, potassium, or magnesium salts. It is believed that the use of a basic addition salt, such as a magnesium salt, will reduce the charge and allow for freer movement of the compound throughout the body. Pyrophosphate compounds, imidopyrophosphate compounds, and the like can be covalently bound to other phosphates creating polyphosphates or polyimidophosphates. One or more pyrophosphate analogs can be administered in combination. In another embodiment, the pyrophosphate analog can be administered with a protective agent. In another embodiment, the pyrophosphate analog can be administered with a neurologic agent, and optionally with a protective agent.

Protective Agents

In another embodiment, the invention provides a method for protecting receptors and/or increasing the efficacy of agents by administering to a subject a protective agent. Protective agents useful in an embodiment of the method of the invention include a bilirubin, biliverdin, carnosol, quercetin, myricetin, a bioflavinoid; a heme binding compound, such as hemopexin, lipopexin, a lipoprotein, or ApoE-2; and a heme oxygenase, such as heme oxygenase-1 or heme oxygenase-2, or biliverdin reductase, a catalase, a peroxidase, a DNA or RNA vector encoding a biliverdin reductase, a DNA or RNA vector encoding a heme oxygenase (e.g. a DNA or RNA vector encoding a heme oxygenase-1 or a DNA or RNA vector encoding a heme oxygenase-2), a DNA or RNA vector encoding a catalase, a DNA or RNA vector encoding a peroxidase, or a combination thereof. Biliverdin reductase is preferably administered with bilirubin, because biliverdin reductase can regenerate bilirubin from biliverdin after bilirubin has been oxidized while functioning as a protective agent. Biliverdin reductase is also preferably administered in combination with a heme oxygenase. Heme oxygenases include recombinant heme oxygenase. Preferably, a heme oxygenase is a human heme oxygenase.

One or more protective agents can be administered in combination. In another embodiment, one or more protective agents can be administered in combination with one or more pyrophosphate analogs. In another embodiment, one or more protective agents can be administered in with one or more neurologic agents, and optionally with one or more pyrophosphate analogs.

Agents that Directly or Indirectly Affect a mAChR

The invention also provides a method for enhancing the efficacy of one or more agents that directly or indirectly affect a mAChR. Agents that directly or indirectly affect a mAChR include agents that (1) bind to or interact with a mAChR to either elicit a response transduced through a mAChR or reduce or prevent an agent from binding to or interacting with a mAChR and/or eliciting a signal transduced through a mAChR, (2) alter the concentration of agents that bind to or interact with a mAChR to either elicit a response transduced through a mAChR or reduce or prevent an agent from binding to or interacting with a mAChR and/or eliciting a signal transduced through a mAChR, or (3) modify the ability of agents that bind to or interact with a mAChR to either elicit a response transduced through a mAChR or reduce or prevent an agent from binding to or interacting with a mAChR and/or eliciting a signal transduced through a mAChR. Such agents include anticholinesterase agents, muscarinic agonists, muscarinic antagonists, and allosteric modifiers of muscarinic receptors. Preferably, the invention provides a method for enhancing the efficacy of agents that either directly or indirectly elicit a response through a mAChR. Most preferably, the method of the invention enhances the efficacy of a muscarinic agonist or an anticholinesterase agent.

Muscarinic receptor agonists directly elicit a response through a mAChR by binding to and transducing a signal through a mAChR. Preferred muscarinic agonists include acetylcholine, Xanomeline, and the like.

A muscarinic antagonist is an agent that is capable of partially or completely inhibiting, or reversing, the effect of a muscarinic agonist on a mAChR. Examples of muscarinic antagonists include atropine, N-methyl-scopolamine, quinuclidinyl benzilate, pirenzepine, and the like.

Cholinesterase hydrolyzes the neurotransmitter acetylcholine and provides one of the mechanisms responsible for rapid depletion of acetylcholine from the synaptic cleft. Anticholinesterase agents inhibit cholinesterase activity and as a result increase the concentration of acetylcholine in the synaptic cleft and prolong the duration of which acetylcholine remains in the synaptic cleft. Anticholinesterase agents can thus indirectly affect a mAChR by increasing concentrations of and prolonging the effective duration of acetylcholine in the synaptic cleft. Anticholinesterase agents can also interact directly with cholinergic receptors, including mAChRs; with sodium and potassium ion channels; and effect the uptake, synthesis and release of neurotransmitters. Preferred anticholinesterase agents include Aricept, Exelon, Metrifonate, and the like.

An allosteric modifier of a mAChR binds or interacts with a site other than the agonist binding site of a mAChR and modifies the ability of an agonist or an antagonist to elicit or inhibit, respectively, a response transduced through a muscarinic receptor, without itself eliciting a response. Suitable allosteric modifiers of a muscarinic agonist include gallamine and dynorphin. Preferred allosteric modifiers of a mAChR include gallamine and dynorphin.

Neurologic Agents

The invention also provides a method for increasing the efficacy of a neurologic agent in a subject in need thereof. In a first embodiment, this method includes administering a pyrophosphate analog. In this embodiment, the increased efficacy of the neurologic agent preferably results from protection of a muscarinic receptor caused or induced by the pyrophosphate analog. In a second embodiment, this method includes administering a protective agent. In this second embodiment, the increased efficacy of the neurologic agent preferably results from protection of a muscarinic receptor caused or induced by the protective agent. In each embodiment, the subject preferably is concurrently receiving, has recently received, or will soon receive a neurologic agent.

A neurologic agent promotes nerve cell growth and survival or augments the activity of functioning cells. Among those agents that are preferred are cholinergic agonists, allosteric modifiers of a mAChR, cholinesterase inhibitors, or neurotrophic and neuritogenic factors that are similar to naturally occurring nerve growth promoting substances. Among the preferred neurologic agents are gangliosides (such as GM-I ganglioside), phosphatidylserine (PS), nerve growth factor (NGF), neurotrophins 3, 4, and/or 5(NT-3, NT-4 and/or NT-5) brain-derived neurotrophic factor (BDNF), fibroblast growth factors (FGFs, e.g., basic fibroblast growth factor), insulin, insulin-like growth factors (IGF-1 and/or IGF-2), ciliary neurotrophic factor (CNTF), transforming growth factors, epidermal growth factors, activity-dependent growth factor, platelet derived growth factor, neuroline, glia-derived neurotrophic factor (GDNF), glia-derived nexin, and cholinergic enhancing factors such as phosphoethanolamine and thyroid hormone T.3, and DNA or RNA vectors or plasmids that encode one or more protein neurologic agents or nerve growth promoting factors. Plasmids and vectors for delivery of a coding sequence to a mammalian tissue are known to those of skill in the art.

Metal Diseases

The method of the invention can treat or prevent diseases or disorders caused or induced by metals, such as cancer and poisoning. Such metals can include As, Co, Cr, Ni, Hg, Pb, Fe, Cu, V, and Cd. That is, the method of the invention can treat or prevent poisoning by (for example) lead or mercury and also excessive iron toxicity. In one embodiment, the method of the invention can treat or prevent CNS diseases or disorders caused or induced by metals. In another embodiment, the method of the invention can treat or prevent diseases or disorders not of the CNS but caused or induced by metals, such as heart disease, blood vessel disease, and gland disease. In another embodiment, the method of the invention reduces poisoning of a subject by at least one metal. In another embodiment, the method of the invention protects a subject from at least one carcinogenic metal. In another embodiment, the method of the invention reduces toxic actions of metal ions in a subject, particularly toxic actions due to $Fe^{++}$, $Hg^{++}$, $Cd^{++}$, $Cu^{++}$, $As^{+++}$, and $Pb^{++}$ ions.

Administering Agents

Administering compounds according to the method of the invention can include formulating the compounds or compositions as pharmaceutical compositions and administering the pharmaceutical compositions to a mammalian host, including a human patient, in a variety of forms adapted to the chosen route of administration. The compounds are preferably administered in combination with a pharmaceutically acceptable carrier. The compounds can be administered at one of a variety of doses sufficient to provide an effective amount at the desired point of action of the agent. Doses for humans and other mammals can range from about 0.001 mg/kg to about 100 mg/kg, preferably from about 0.01 mg/kg to about 10 mg/kg, preferably from about 0.1 mg/kg to about 1-10 mg/kg.

A related use of the methods of the invention is to protect pharmacological agents in formulation. The pharmacological agents may be for therapeutic, diagnostic, or other purposes.

The compounds can be administered by known techniques, such as orally, intranasally, parentally (including subcutaneous injection, intravenous, intramuscular, intrasternal or infusion techniques), by inhalation spray, dermally, transdermally, intrathecal, intracerebroventricular, buccal, sublingual, topically, by absorption through a mucous membrane or through the skin, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, eye drops, nose drops, creams, sterile injectable preparations, such as sterile injectable aqueous or oleagenous suspensions or suppositories.

Controlled or sustained release systems can also be employed. For example, compositions can include a polymer or other substance that enhances controlled or sustained release. Controlled or sustained release systems can include a polymer disk, such as evac disks, microspheres, and copolymers. Preferred controlled release polymers are poly(lactide:glycolide) and poly(ethylene-co-vinyl acetate).

For oral administration as a suspension, the compositions can be prepared according to techniques well known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

In addition to the typical pharmacological methods for oral administration, the agents employed in the methods of the invention can be administered as a component of a nutritional or food supplement. The nutritional or food supplement can also include any other ingredients typical of a nutritional or food supplement, such as flavorings, stabilizers, and the like.

For administration by inhalation or aerosol, the compositions can be prepared according to techniques well known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For intranasal administration, the compositions can be formulated according to techniques well known in the art. The means of applying a pharmaceutical composition intranasally can be in a variety of forms such as a powder, spray or nose drops.

For transdermal administration, the compositions can be formulated according to techniques well known in the art. Delivery of the composition through the skin can be accomplished by delivery means well known in the art, including transdermal patch, an ointment, an iontophoretic patch or device, and the like.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes.

Intraocular administration through the use of an ointment or eye drops is preferred for treatment of a glandular disease or disorder of the eye, such as a lachrymal gland disease disorder like Sjogren's Syndrome or dry eye syndrome.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders including an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium including, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monostearate hydrogels and gelatin.

Sterile injectable solutions are prepared by incorporating the compounds in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Administering Agents to the Brain

Administering agents, e.g. a protective agent, a pyrophosphate analog, an agent that directly or indirectly affects a mAChR, and/or a neurologic agent, according to the method of the invention includes administering agents to a mammalian host in a manner that allows the agents to exert their effect in the CNS. Many agents useful for the method of the invention can be absorbed into the blood stream and readily cross the blood brain barrier.

However, some agents useful for the method of the invention cannot pass, or have difficulty passing, the blood brain barrier. Such agents can be administered as "prodrugs" which can cross the blood brain barrier, and upon or after entry into the CNS, the prodrug is converted to the active agent. Agents that can cross the blood brain barrier without difficulty can also be administered as prodrugs.

To deliver the agent to the CNS, the agent alone or in combination with other substances as a pharmaceutical composition may be administered to the spinal cord and to the cerebral vesicles according to intrathecal and intracerebrovascular administration methods known in the art. Such pharmaceutical compositions can also be administered to the nasal cavity, under the tongue, or onto the eye. The composition may be dispensed intranasally, sublingually, or conjunctivally as a powdered or liquid nasal spray, nose drops, a gel or ointment, through a tube or catheter, by syringe, by packtail, by pledget, or by submucosal infusion. The agent may be combined with a polymer or other substance that enhances controlled or sustained release of the agent. In particular, agents can be delivered to the brain by intranasal administration as described in X.-Q. Chen et al. (1998) J. Alzheimer's Disease 1:35-44 and W. H. Frey II et al. (1997) Drug Delivery 4:87-92; the disclosures of which are incorporated herein by reference.

The optimal concentration of the active agent will necessarily depend upon the specific agent used, the characteristics of the patient and the nature of the disease or condition for which the treatment is to be used.

The carrier of the composition may be any material which is otherwise pharmaceutically-acceptable. and compatible with the active ingredients of the composition. Where the carrier is a liquid, it is preferred that the carrier is hypotonic or isotonic with nasal, oral, or conjunctival fluids and have a pH within the range of 4.5-7.5. Where the carrier is in powdered form, it is preferred that the carrier is also within an acceptable non-toxic pH range.

The pharmaceutical composition may be formulated as a powder, granules, solution, ointment, cream, aerosol, powder, drops, or a controlled or sustained release composition such as a polymer disk. The solution may be sterile, isotonic or hypotonic, and otherwise suitable for administration by injection or other means. In addition to the agent, the solution may contain appropriate adjuvants, buffers, preservatives and salts. The powder or granular forms of the pharmaceutical composition may be combined with a solution and with diluting, dispersing or surface active agents. Solutions such as nose or eye drops may contain an antioxidant, a buffer, and the like. Further controlled release polymers may be used to regulate the delivery of the agent.

The present invention may be better understood with reference to the following examples. These examples are intended to be representative of specific embodiments of the invention, and are not intended as limiting the scope of the invention.

EXAMPLES

Example 1

Protection of Muscarinic Acetylcholine Receptor (mAChR) in Cell Free Systems

Materials and Methods

Membrane mAChR Preparation

Membranes rich in mAChRs were prepared by a modification of the method used by Marks and Collins (Characterization of nicotine binding in mouse brain and comparison with the binding of a-bungarotoxin and quinuclindinyl benzilate, Mol. Pharmacol. 22:544-564, 1982). Gray matter from nondemented adult human frontal cortex was homogenized in 9 vol of 50 mM Tris-HCl, pH 7.4, using 5 passes of a glass/Teflon motor-driven homogenizer. The homogenate was centrifuged at 27 000×g for 20 mm at 4° C., and the subsequent pellet resuspended in 9 vol of cold deionized water with 5 passes of the homogenizer. The resuspension was incubated at 37° C. for 5 min, then was centrifuged as before. The resulting pellet was resuspended, incubated and centrifuged again as above. The final pellet was weighed, resuspended at 15% w/v in 50 mM Tris-HCl buffer, aliquoted in small portions, flash-frozen in liquid nitrogen and stored at −70° C. for subsequent assays to determine content and binding capacity. Before use in binding assays, the thawed membrane preparation was briefly rehomogenized with 10 passes in a glass/glass homogenizer. A typical mAChR membrane preparation bound 300 pmol [$^3$H] quinuclidinyl benzilate ([$^3$H]QNB)/g protein.

Inhibitor Preparation

Gray matter obtained from the frontal cortex of cases with AD was homogenized in 9 vol of 1% trifluoroacetic acid (TFA) for 40 s at 4° C. in a Waring blender, then centrifuged at 1200×g for 10 min at 4° C. The resulting supernatant fraction was centrifuged at 11 000×g for 100 min at 4° C. The 11 000×g supernatant fraction was centrifuged at 100 000×g for 100 min at 4° C., then the 100 000×g supernatant fraction was concentrated using a SpeedVac and resuspended in 0.1% TFA to half the original tissue volume. The 100 000×g supernatant fraction was transferred to a Spectra/Por 3 dialysis membrane bag (3500 dalton cutoff), and dialyzed against 20 vol of 0.1% TFA at 4° C. for 24 h with gentle stirring. The resulting <3500 Da fraction (dialysate) was concentrated by SpeedVac to half the original tissue volume. The <3500 Da fraction (endogenous inhibitor) was then frozen in liquid nitrogen and stored at −70° C. for subsequent assays to determine protein count and inhibitor activity. Protein activity was measured using the bicinchononic acid (BCA) protein assay method, essentially as described by Smith et al. (Measurement of protein binding using bicinchonic acid, Ann. Biochem. 150: 76-85, 1985). A typical inhibitor preparation contained about 4 mg/ml protein and approximately twice the concentration of inhibitor found in the original tissue.

Inhibitor Activity Assay

Inhibitor activity was measured using a modification of the method of Fields et al. (Cardiac muscarinic receptors, J. Biol. Chem. 253:3251-3258, 1978) to assess the binding of [$^3$H] QNB, a mAChR antagonist, or [$^3$H]-oxotremorine M, a mAChR agonist. In general, binding conditions consisted of 50 mM Tris-HCl, pH 7.4 at 37° C., 10 mM reduced glutathione (GSH), 75μ/ml membrane and 2×10$^{-10}$ M [$^3$H]QNB or 3 nM [$^3$H]-oxotremorine M, with and without addition of inhibitor. To control for non-specific binding, 12.5 μM atropine sulfate (a mAChR antagonist) was added to several tubes. Subtracting nonspecific binding from total binding yielded specific binding.

Pyrophosphate, imidodiphosphate, adenylylimidodiphosphate, guanylimidodiphosphate, and tripylyphosphate were dissolved in distilled water. Bilirubin, biliverdin, and heme were dissolved in DMSO. Carnosol, myricetin, and quercetin were dissolved in ethanol. Catalase and peroxidase were dissolved in an aqueous, preferably buffered, solution.

Enough water was added to all other reaction components in each tube to make 4 ml total. The binding reaction was initiated by adding [$^3$H]QNB or [$^3$H]-oxotremorine-M, mixing the tubes briefly, and then incubating the tubes at 37° C. for [$^3$H]QNB or at room temperature for [$^3$H]-oxotremorine-M. The reaction time for [$^3$H]QNB was one hour in most experiments. In some experiments, the mAChR was preincubated with either the endogenous LMW inhibitor or heme plus peroxide in the presence or absence of the therapeutic agent being tested. The effect of the therapeutic agent on receptor function was then assessed in a binding assay, which for [$^3$H]QNB was conducted at 37° C. for 40 min, and for [$^3$H]-oxotremorine-M was conducted at room temperature for 20 min. After 60 min, the binding reaction was terminated by adding 5 ml of cold 50 mM Tris buffer, pH 7.4, to each tube and chilling the tubes in an ice bath. The tube contents and one 15 ml rinse of cold 50 mM Tris buffer, pH 7.4, were filtered through Whatman GF/B glass fiber filters using a Brandel harvester. The filters were placed in Optiflour scintillation flour and counted in a Beckman LS-6500 scintillation counter set for tritium detection.

Results

The data resulting from the methods presented above and the results presented in FIGS. 1-20 are discussed in more detail below.

Figure 3:
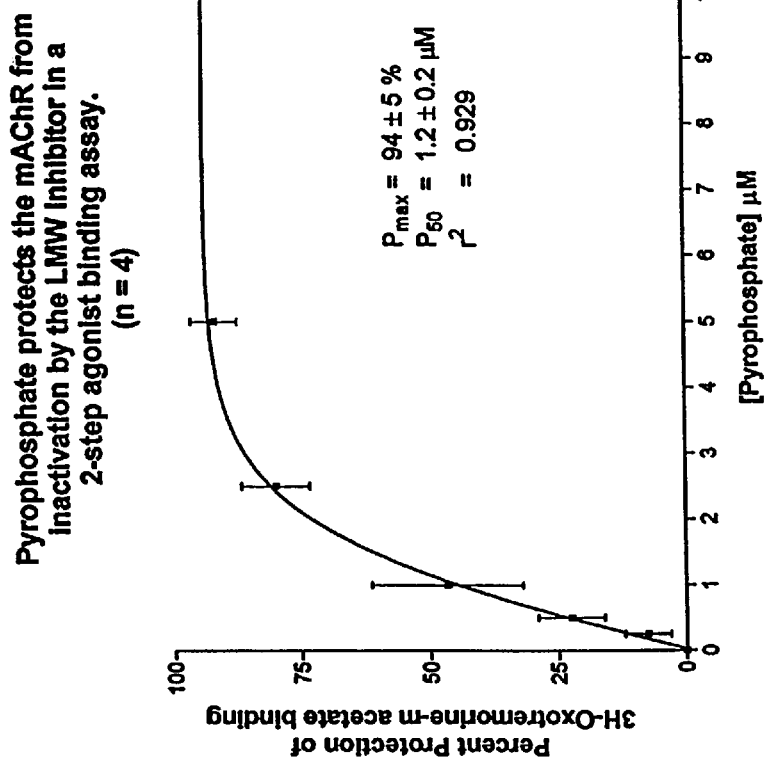
FIG. 3 illustrates protection of a mAChR by pyrophosphate. Pyrophosphate protected the mAChR from inactivation by the endogenous low molecular weight inhibitor. Pyrophosphate protected the receptor from loss of agonist (oxotremorine) binding.
Figure 4:
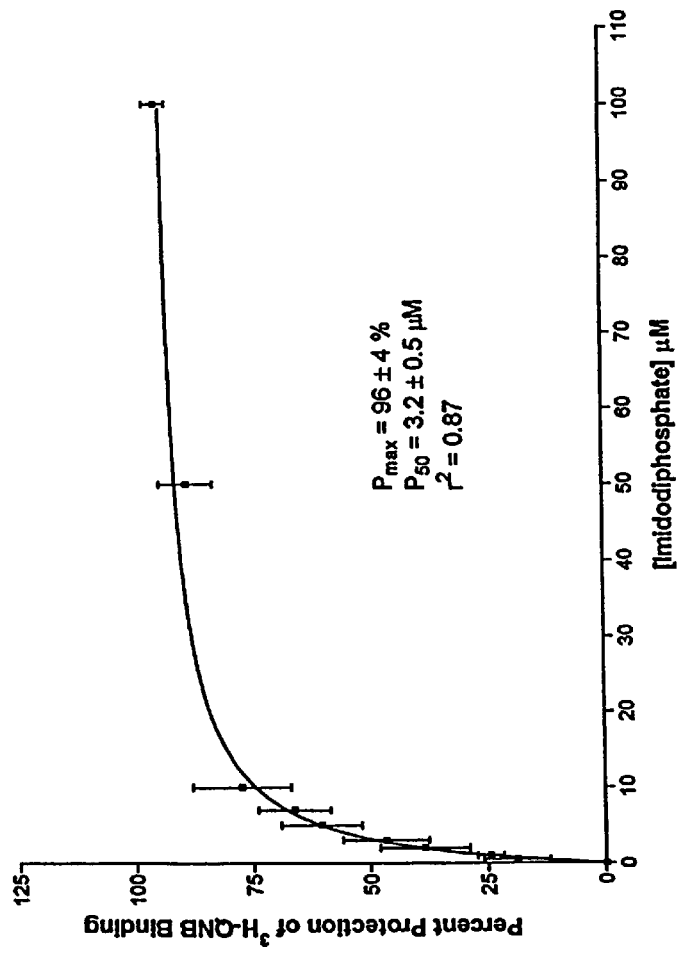
FIG. 4 illustrates protection of a mAChR by imidodiphosphate. Imidodiphosphate protected the mAChR from inactivation by the endogenous low molecular weight inhibitor. Imidodiphosphate protected the receptor from loss of antagonist ($^3$H-QNB) binding.
Figure 6:
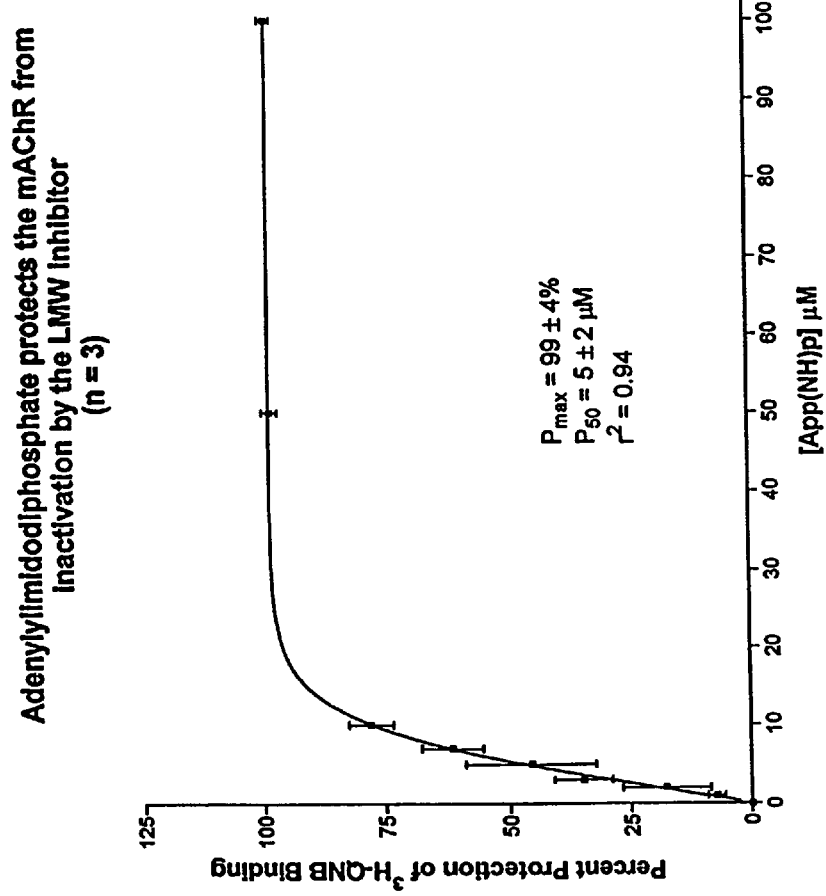
FIG. 6 illustrates protection of a mAChR by adenylylimidodiphosphate. Adenylylimidodiphosphate protected the mAChR from inactivation by the endogenous low molecular weight inhibitor. Adenylylimidodiphosphate protected the receptor from loss of antagonist ($^3$H-QNB) binding.
Figure 7:
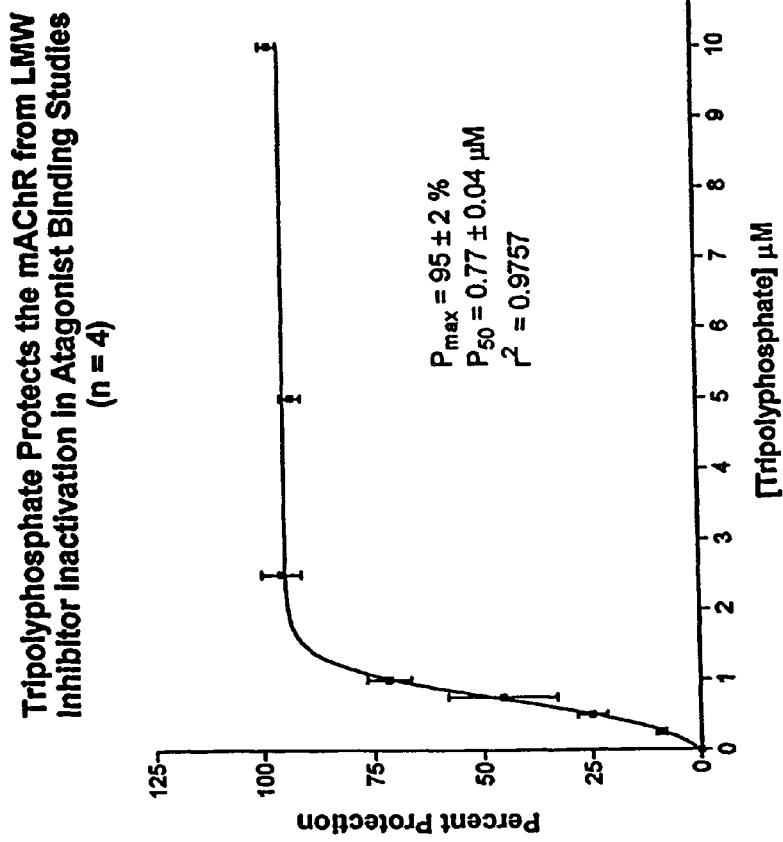
FIG. 7 illustrates protection of a mAChR by tripolyphosphate. Tripolyphosphate protected the mAChR from inactivation by the endogenous low molecular weight inhibitor. Tripolyphosphate protected the receptor from loss of antagonist ($^3$H-QNB) binding.
Figure 8:
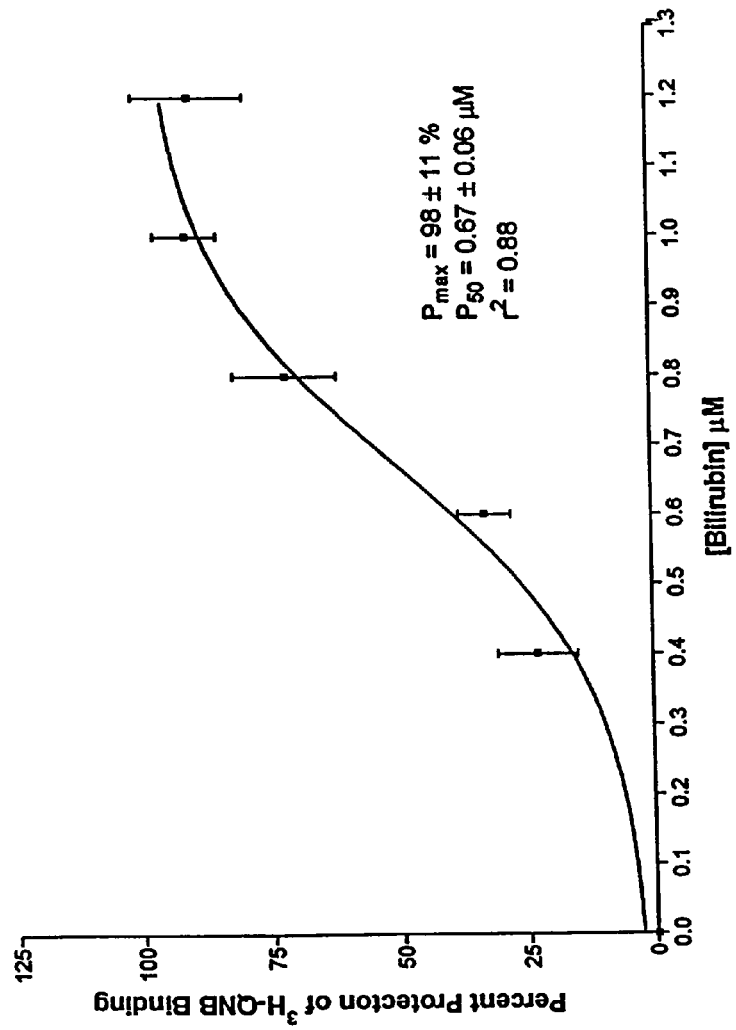
FIG. 8 illustrates protection of a mAChR by bilirubin. Bilirubin protected the mAChR from inactivation by the endogenous low molecular weight inhibitor. Bilirubin protected the receptor from loss of antagonist ($^3$H-QNB) binding.
Figure 9:
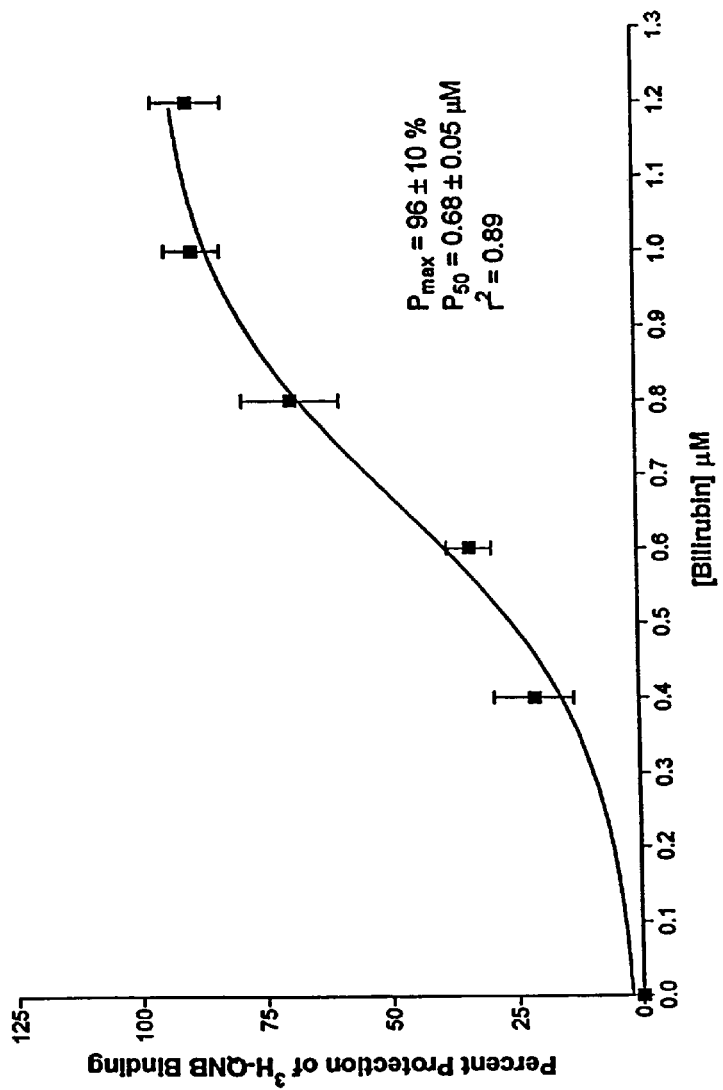
FIG. 9 illustrates protection of a mAChR by bilirubin. Bilirubin protected the mAChR from inactivation by heme and peroxide. Bilirubin protected the receptor from loss of antagonist ($^3$H-QNB) binding.
Figure 20:
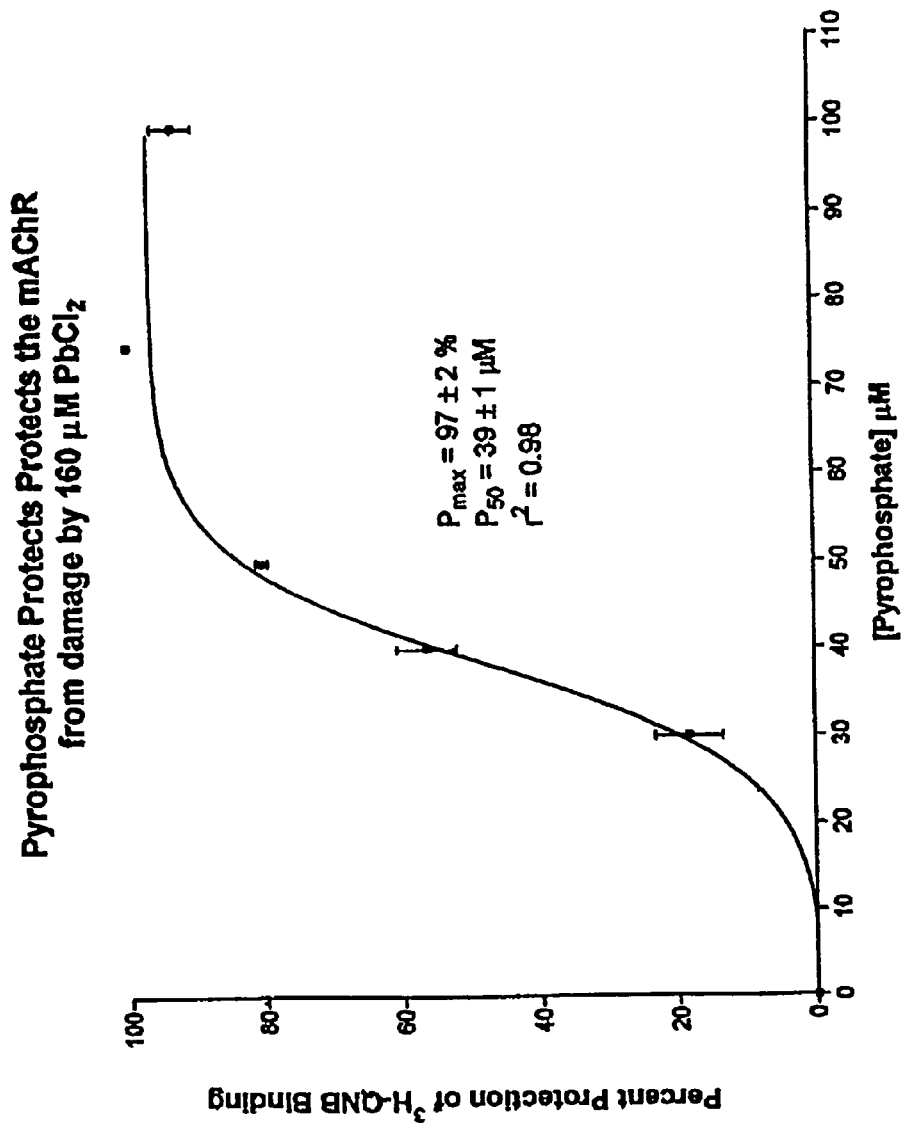
FIG. 20 illustrates protection of a mAChR by pyrophosphate. Pyrophosphate protected the mAChR from damage by the metal lead in the form of $PbCl_2$. Pyrophosphate protected the receptor from loss of antagonist ($^3$H-QNB (quinulidinyl benzilate)) binding.

Pyrophosphate:

Pyrophosphate protects the mAChR from inactivation by the LMW inhibitor or by the combination of heme and peroxide. Pyrophosphate protected the receptor from both loss of antagonist ($^3$H-QNB) binding (FIGS. 1 and 2) and agonist ($^3$H-Oxotremorine M) binding (FIG. 3). Approximately 1 μM pyrophosphate provides 50% protection. Pyrophosphate also protects the mAChR from damage by $PbCl_2$. Approximately 57 μM pyrophosphate provides 50% protection (FIG. 20).

Imidodiphosphates:

imidodiphosphate (FIG. 4), guanylimidodiphosphate (FIG. 5), and adenylylimidodiphosphate (FIG. 6) all protect the mAChR from inactivation by the LMW inhibitor.

Polyphosphates:

Polyphosphates, such as tripolyphosphate (FIG. 7), protect the mAChR from inactivation by the LMW inhibitor.

Bisphosphonates:

Bisphosphonates, such as pamidronate (FIG. 19), protect the mAChR from inactivation by the LMW inhibitor.

Figure 10:
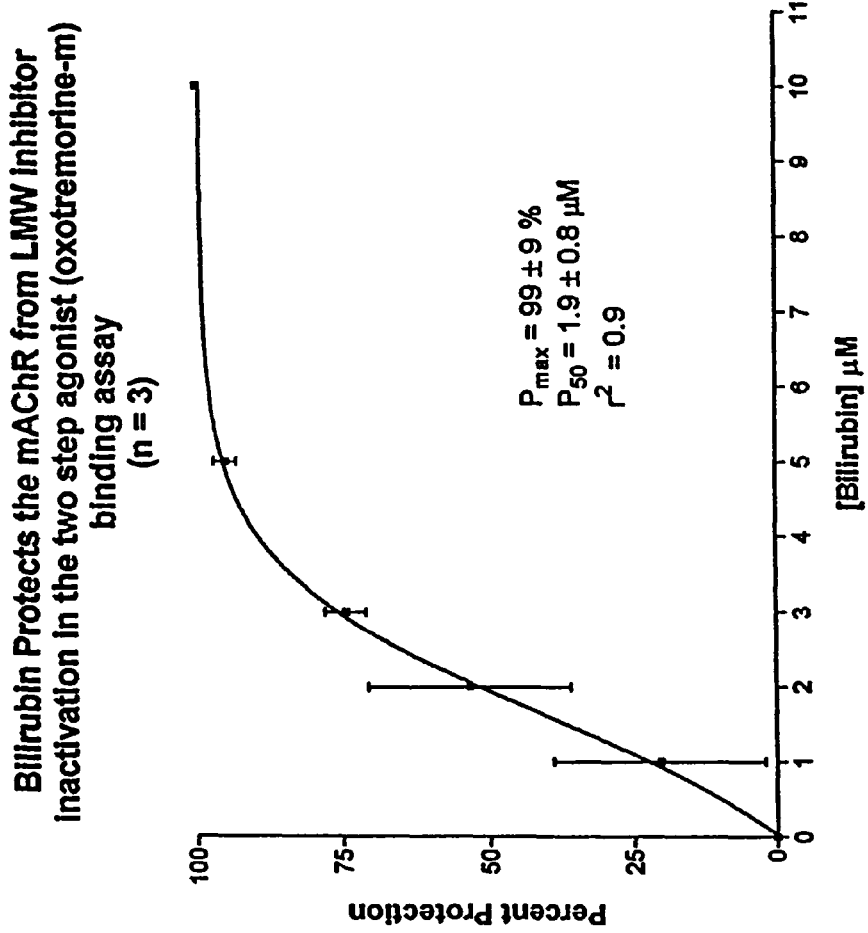
FIG. 10 illustrates protection of a mAChR by bilirubin. Bilirubin protected the mAChR from inactivation by the endogenous low molecular weight inhibitor. Bilirubin protected the receptor from loss of agonist (oxotremorine) binding.
Figure 11:
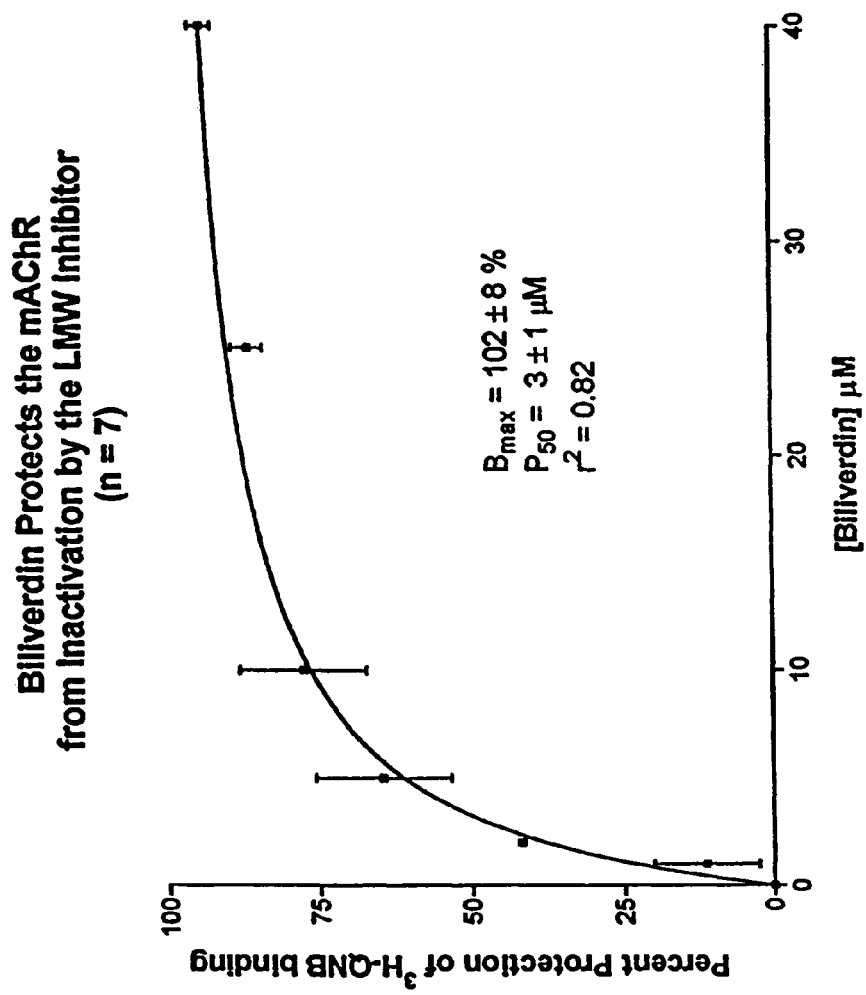
FIG. 11 illustrates protection of a mAChR by biliverdin. Biliverdin protected the mAChR from inactivation by the endogenous low molecular weight inhibitor. Biliverdin protected the receptor from loss of antagonist ($^3$H-QNB) binding.
Figure 12:
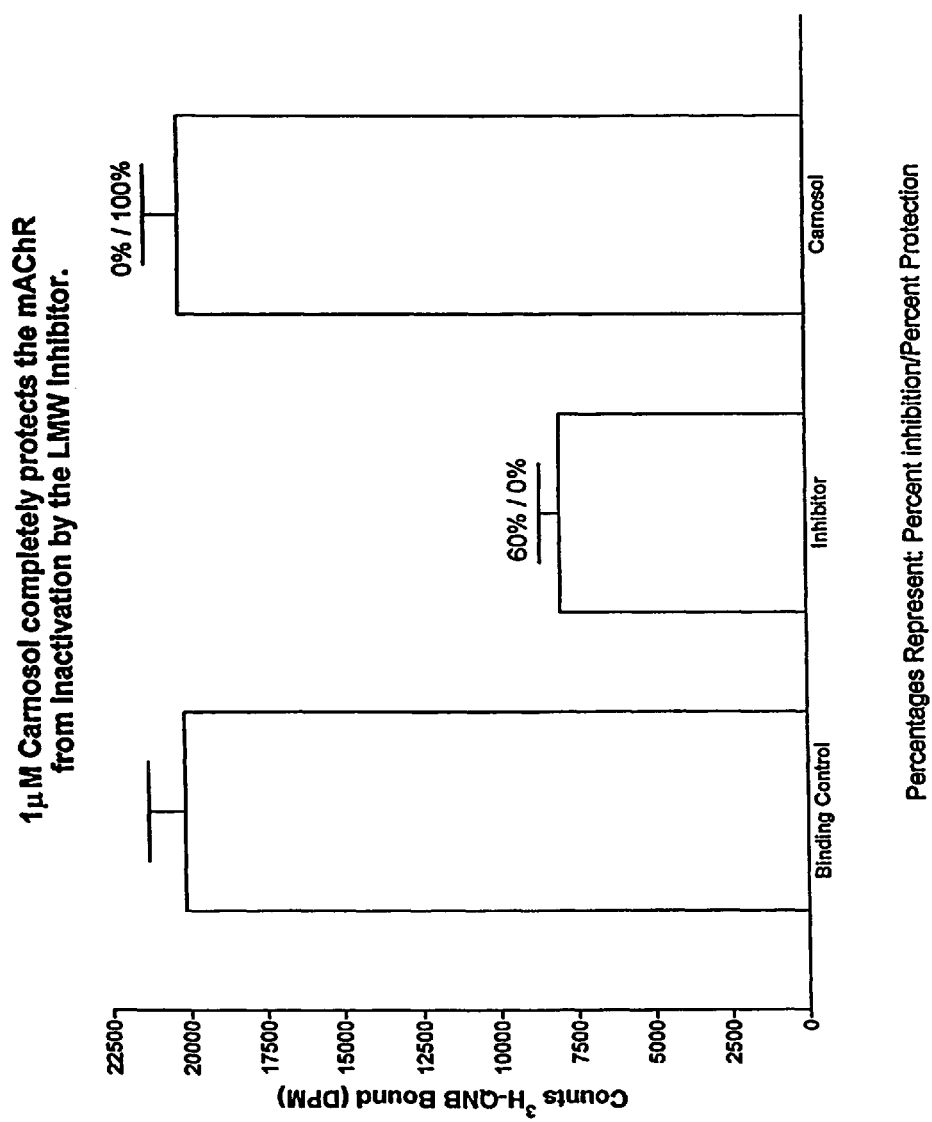
FIG. 12 illustrates protection of a mAChR by carnosol, Carnosol protected the mAChR from inactivation by the endogenous low molecular weight inhibitor. Carnosol protected the receptor from loss of antagonist ($^3$H-QNB) binding.
Figure 13:
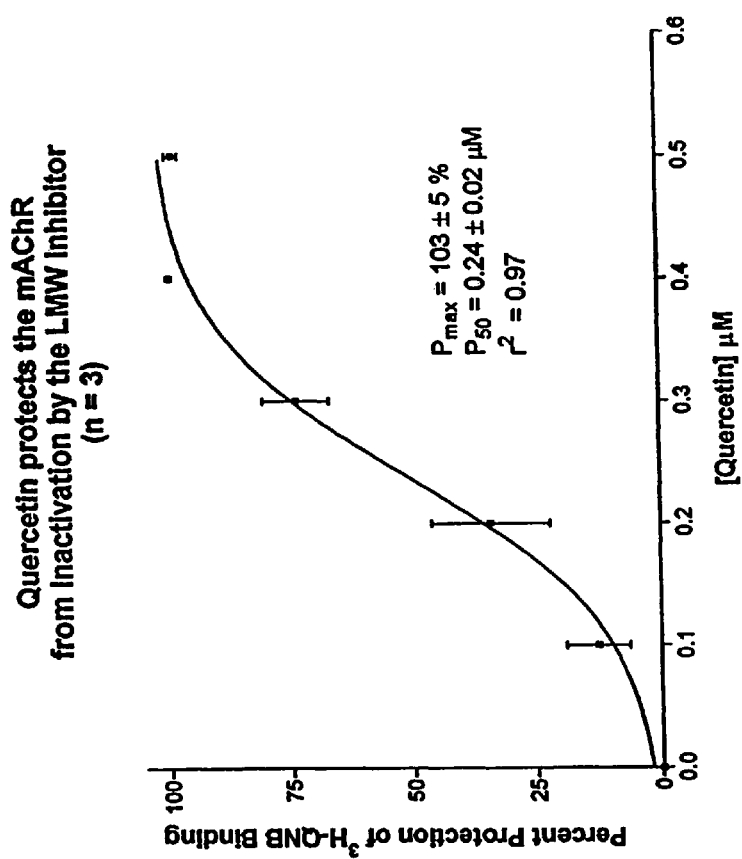
FIG. 13 illustrates protection of a mAChR by quercetin. Quercetin protected the mAChR from inactivation by the endogenous low molecular weight inhibitor. Quercetin protected the receptor from loss of antagonist ($^3$H-QNB) binding.
Figure 14:
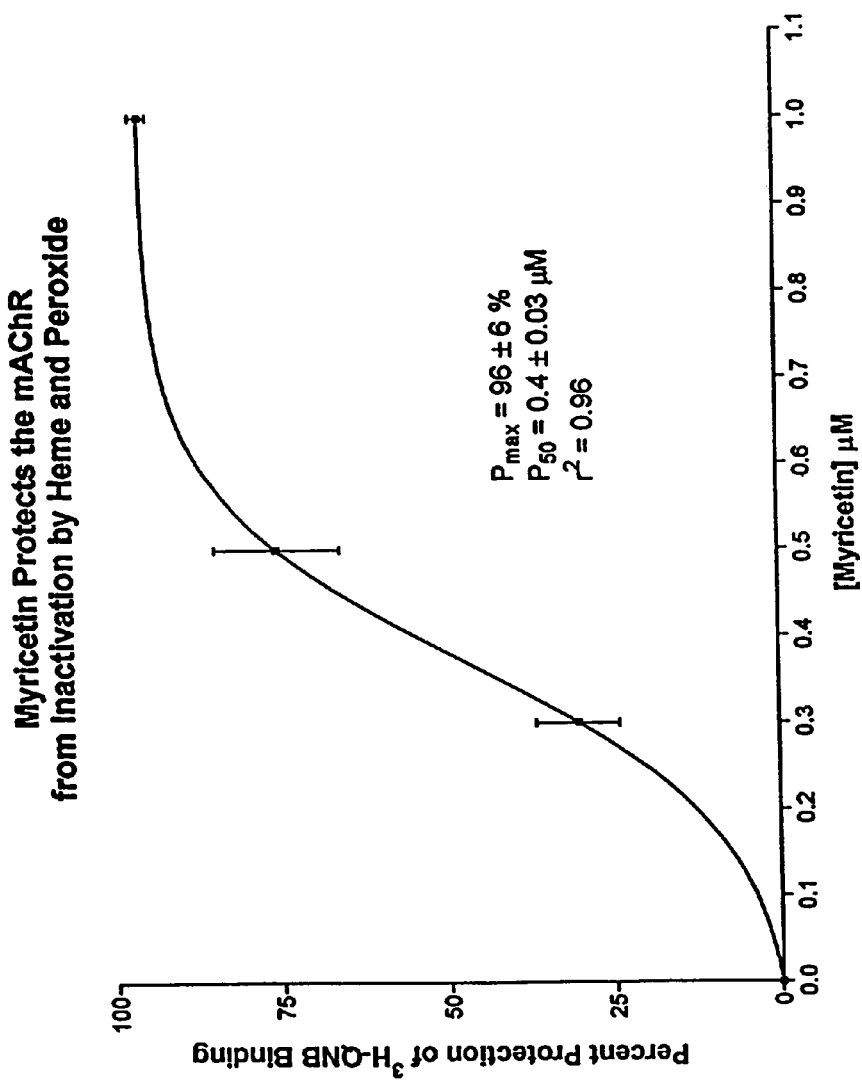
FIG. 14 illustrates protection of a mAChR by myricetin. Myricetin protected the mAChR from inactivation by the endogenous low molecular weight inhibitor. Myricetin protected the receptor from loss of antagonist ($^3$H-QNB) binding.

Bilirubin and Biliverdin:

Bilirubin protects the mAChR from inactivation by the LMW inhibitor or by the combination of heme and peroxide. Approximately 0.7 μM bilirubin provides 50% protection of the receptor from loss of antagonist ($^3$H-QNB) binding (FIGS. 8 and 9) and 1.9 μM provides 50% protection from loss of agonist ($^3$H-Oxotremorine M) binding (FIG. 10).

biliverdin at 3 μM provides 50% protection of the mAChR (FIG. 11).

Carnosol, Quercetin, and Myricetin:

Carnosol (FIG. 12), quercetin (FIG. 13), and myricetin (FIG. 14) all protected the mAChR from inactivation. Carnosol provided 100% protection at 1 μM. while quercetin and myricetin provided 50% protection at 0.24 μM and 0.4 μM respectively.

Catalase and Peroxidase

Figure 15:
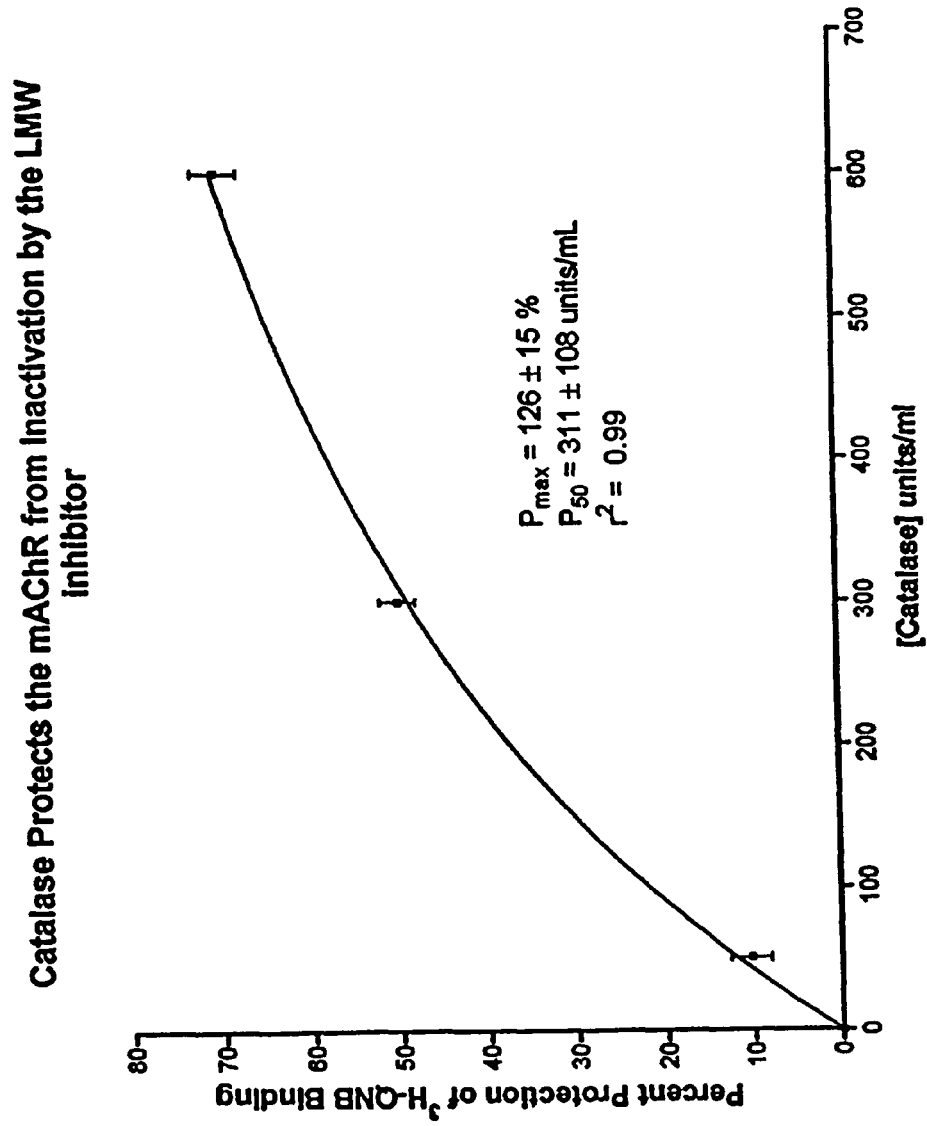
FIG. 15 illustrates protection of a mAChR by catalase. Catalase protected the mAChR from inactivation by the endogenous low molecular weight inhibitor. Catalase protected the receptor from loss of antagonist ($^3$H-QNB) binding.
Figure 16:
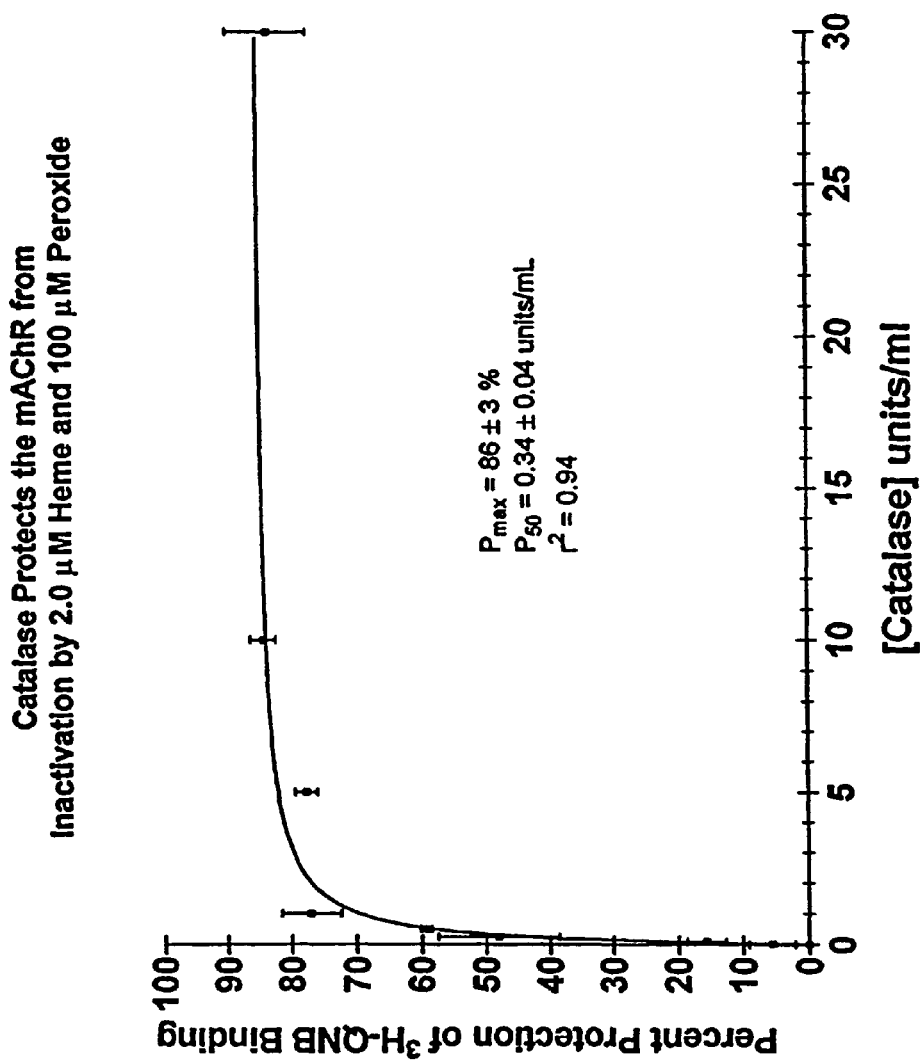
FIG. 16 illustrates protection of a mAChR by catalase. Catalase protected the mAChR from inactivation by heme and peroxide. Catalase protected the receptor from loss of antagonist ($^3$H-QNB) binding.

Catalase protected the mAChR from inactivation by the LMW inhibitor or by the combination of heme and peroxide (FIGS. 15 and 16, respectively). As little as 0.34 units/mL of catalase provided 50% protection from inactivation by heme and peroxide.

Figure 17:
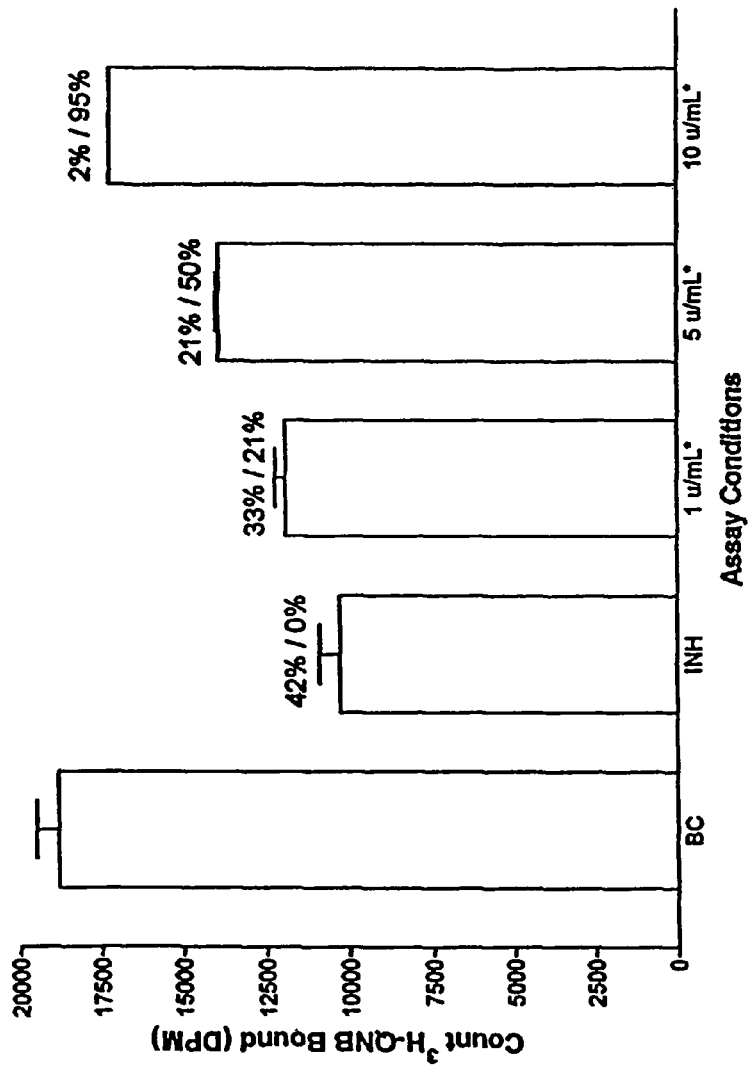
FIG. 17 illustrates protection of a mAChR by a peroxidase. The peroxidase protected the mAChR from inactivation by the endogenous low molecular weight inhibitor. The peroxidase protected the receptor from loss of antagonist ($^3$H-QNB) binding.
Figure 18:
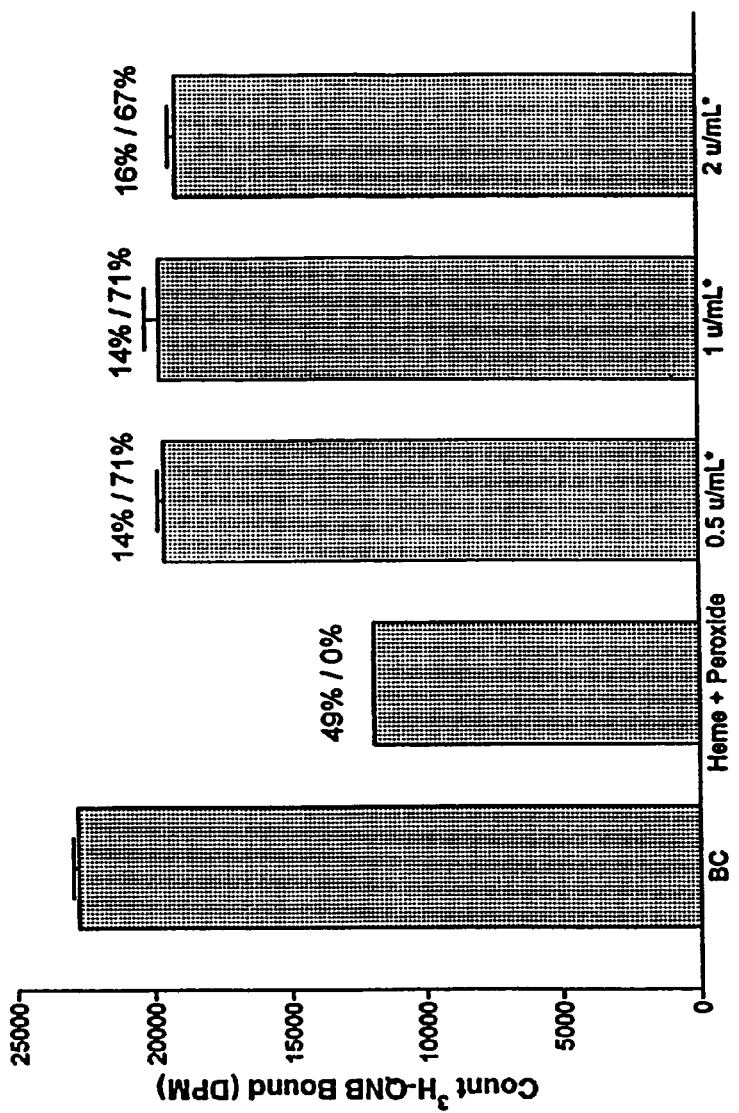
FIG. 18 illustrates protection of a mAChR by a peroxidase. The peroxidase protected the mAChR from inactivation by heme and peroxide. The peroxidase protected the receptor from loss of antagonist ($^3$H-QNB) binding.
Figure 19:
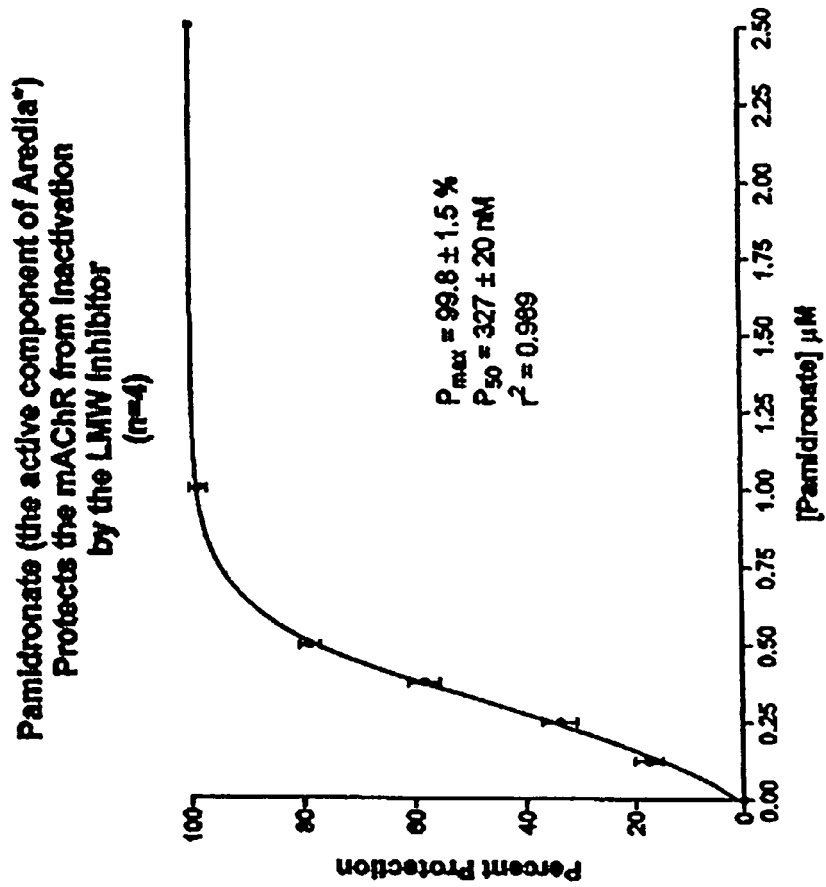
FIG. 19 illustrates protection of mAChR by pamidronate. Panidronate protected the mAChR from inactivation by the endogenous low molecular weight inhibitor.

A peroxidase, specifically glutathione peroxidase, protected the mAChR from inactivation by the LMW inhibitor or by the combination of heme and peroxide (FIGS. 17 and 18, respectively). Glutathione peroxidase at 0.5 units/mL provided 71% protection from inactivation by heme and peroxide.

Conclusion

The results indicate that pyrophosphate, imidodiphosphates, polyphosphates, bisphosphonates, bilirubin, biliverdin, carnosol, quercetin and myricetin protect a receptor and increase the ability of agents to bind a receptor. Particularly, the results demonstrate the ability of these agents to protect a muscarinic receptor from the effects of endogenous LMW inhibitor, heme and metals and increase the ability of muscarinic agonists and antagonists to bind a mAChR, suggesting that these agents can be used effectively to protect other receptors and increase the efficacy of other agents.

Because the mAChR is essential for memory and learning, the specific demonstration that these agents can protect the human brain mAChR from inactivation and increase agonist binding indicates that these agents have therapeutic potential for the treatment of cognitive and memory disorders including those associated with aging, such as Alzheimer's disease.

Example 2

Protection of the mAChR in Cell Culture

Various systems for determining the protection of a mAChR in cell culture are known in the art. Such cell culture systems can be used to determine if mAChR is protected from a damaging agent or condition according to the method of the invention. For example, by administering a mAChR antagonist or agonist alone or in combination with one or more protective agent and/or one or more pyrophosphate analog, one of skill in the art can determine if a mAChR is protected by the one or more protective agent and/or one or more pyrophosphate analog.

Example 3

Protection of the mAChR Receptor in Animals

Various systems for determining the protection of a mAChR in animals are known in the art. Such animal systems can be used to determine if mAChR is protected according to the method of the invention. For example, by administering a mAChR antagonist or agonist alone or in combination with one or more protective agents and/or one or more pyrophosphate analogs, one of skill in the art can determine if a mAChR is protected by the one or more protective agents and/or one or more pyrophosphate analogs.

Example 4

Increased Efficacy of Neurologic Agents in Model Systems

Various models systems for determining the efficacy of neurologic agents are known in the art. Such model systems can be used to determine if the efficacy of a neurologic agent is increased by the method of the invention. For example, by administering one or more neurologic agents alone or in combination with one or more protective agents and/or one or more pyrophosphate analogs, one of skill in the art can determine if the efficacy of the one or more neurologic agents is increased when administered with one or more protective agents and/or one or more pyrophosphate analogs within the parameters of the model system according to techniques known in the art.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

We claim:

1. A method for protecting muscarinic receptors in the central nervous system of a patient from inactivation, comprising:
   intranasally administering an effective amount of at least one protective agent, wherein the at least one protective agent comprises myricetin;
   thereby enabling the effective amount of the at least one protective agent to bypass the blood-brain barrier;
   delivering the effective amount of the at least one protective agent directly to the muscarinic receptors within the central nervous system; and
   protecting the muscarinic receptors from inactivation.

2. The method of claim 1, wherein the effective amount of the at least one protective agent administered to the subject is within the range of about 0.001 mg/kg to about 100 mg/kg.

3. The method of claim 1, wherein the effective amount of the at least one protective agent administered to the subject is within the range of about 0.01 mg/kg to about 10 mg/kg.

4. The method of claim 1, wherein the effective amount of the at least one protective agent administered to the subject is within the range of about 0.1 mg/kg to about 1 mg/kg.

5. The method of claim 1, further comprising:
   intranasally administering the effective amount of the at least one protective agent;
   administering an effective amount of at least one neurologic agent;
   thereby enabling the effective amounts of the at least one protective agent to bypass the blood-brain barrier;
   delivering the effective amount of the at least one protective agent directly to the muscarinic receptors; and
   protecting the muscarinic receptors from inactivation.

6. The method of claim 5, further comprising administering at least one neurologic agent with at least one of a bilirubin, biliverdin, carnosol, quercetin, myricetin, a bioflavinoid, a combination thereof, or a pharmaceutically acceptable salt thereof.

7. The method of claim 5, further comprising administering heme oxygenase, a vector encoding a heme oxygenase, heme oxygenase-1, a vector encoding a heme oxygenase-1, heme oxygenase-2, a vector encoding a heme oxygenase-2, a biliverdin reductase, a vector encoding a biliverdin reductase, a catalase, a vector encoding a catalase, a peroxidase, a vector encoding a peroxidase, or a combination thereof.

8. The method of claim 5, further comprising administering a heme binding protein.

9. The method of claim 8, wherein the heme binding protein comprises hemopexin, a lipoprotein, or a combination thereof.

10. The method of claim 5, wherein the at least one neurologic agent further comprises cholinergic agonists, allosteric modifers of a muscarinic receptor, cholinesterase inhibitors, neurotrophic factors, and neuritogenic factors.

11. The method of claim 10, wherein the at least one neurologic agent further comprises gangliosides, phosphatidylserine, nerve growth factor, neurotrophins 3, 4, and/or 5, brain-derived neurotrophic factor, fibroblast growth factors, insulin, insulin-like growth factors, ciliary neurotrophic factor, transforming growth factors, epidermal growth factors, activity-dependent growth factor, platelet derived growth factor, neurokine, glia-derived growth factor, phosphoethanolamine, thyroid hormone T.3, and DNA or RVA vectors or plasmids that encode protein neurologic agents or nerve growth promoting factors.

12. The method of claim 5, wherein the intranasal administration of the effective amount of the at least one protective agent increases the efficacy of the at least one neurologic agent.

13. The method of claim 5, wherein the effective amount of the at least one protective agent administered to the subject is within the range of about 0.001 mg/kg to about 100 mg/kg.

14. The method of claim 5, wherein the effective amount of the at least one protective agent administered to the subject is within the range of about 0.01 mg/kg to about 10 mg/kg.

15. The method of claim 5, wherein the effective amount of the at least one protective agent administered to the subject is within the range of about 0.1 mg/kg to about 1 mg/kg.

16. The method of claim 1, wherein the protected muscarinic receptors are in the central nervous system of a patient with Alzheimer's disease.

17. A method for treating muscarinic receptors in the central nervous system of a subject patient from inactivation, comprising:
   intranasally administering an effective amount of myricetin;
   thereby enabling the effective amount of myricetin to bypass the blood-brain barrier;
   delivering the effective amount of myricetin directly to the muscarinic receptors within the central nervous system; and
   treating the muscarinic receptors.

18. The method of claim 17, wherein the effective amount of the at least one protective agent administered to the subject is within the range of about 0.001 mg/kg to about 100 mg/kg.

19. The method of claim 17, wherein the effective amount of the at least one protective agent administered to the subject is within the range of about 0.01 mg/kg to about 10 mg/kg.

20. The method of claim 17, wherein the effective amount of the at least one protective agent administered to the subject is within the range of about 0.1 mg/kg to about 1 mg/kg.

21. The method of claim 17, further comprising:
   intranasally administering the effective amount of myricetin;
   administering an effective amount of at least one neurologic agent;
   thereby enabling the effective amount of myricetin to bypass the blood-brain barrier;
   delivering the effective amount of myricetin directly to the muscarinic receptors; and
   treating the muscarinic receptors.

22. The method of claim 17, further comprising administering at least one neurologic agent with at least one of a bilirubin, biliverdin, carnosol, quercetin, myricetin, a bioflavinoid, a combination thereof, or a pharmaceutically acceptable salt thereof.

23. The method of claim 17, further comprising administering heme oxygenase, a vector encoding a heme oxygenase, heme oxygenase-1, a vector encoding a heme oxygenase-1, heme oxygenase-2, a vector encoding a heme oxygenase-2, a biliverdin reductase, a vector encoding a biliverdin reductase, a catalase, a vector encoding a catalase, a peroxidase, a vector encoding a peroxidase, or a combination thereof.

24. The method of claim 17, further comprising administering a heme binding protein.

25. The method of claim 24, wherein the heme binding protein comprises hemopexin, a lipoprotein, or a combination thereof.

26. The method of claim 17, wherein the at least one neurologic agent further comprises cholinergic agonists, allosteric modifers of a muscarinic receptor, cholinesterase inhibitors, neurotrophic factors, and neuritogenic factors.

27. The method of claim 17, wherein the at least one neurologic agent further comprises gangliosides, phosphatidylserine, nerve growth factor, neurotrophins 3, 4, and/or 5, brain-derived neurotrophic factor, fibroblast growth factors, insulin, insulin-like growth factors, ciliary neurotrophic factor, transforming growth factors, epidermal growth factors, activity-dependent growth factor, platelet derived growth factor, neurokine, glia-derived growth factor, phosphoethanolamine, thyroid hormone T.3, and DNA or RVA vectors or plasmids that encode protein neurologic agents or nerve growth promoting factors.

28. The method of claim 17, wherein the intranasal administration of the effective amount of myricetin increases the efficacy of the at least one neurologic agent.

29. The method of claim 17, wherein the effective amount of myricetin administered to the subject is within the range of about 0.001 mg/kg to about 100 mg/kg.

30. The method of claim 17, wherein the effective amount of myricetin administered to the subject is within the range of about 0.01 mg/kg to about 10 mg/kg.

31. The method of claim 17, wherein the effective amount of myricetin administered to the subject is within the range of about 0.1 mg/kg to about 1 mg/kg.

32. The method of claim 17, wherein the treated muscarinic receptors are in the central nervous system of a patient with Alzheimer's disease.

* * * * *